United States Patent [19]

Lawrence et al.

[11] Patent Number: 5,571,684
[45] Date of Patent: *Nov. 5, 1996

[54] ASSAY FOR PROLINE IMINOPEPTIDASE AND OTHER HYDROLYTIC ACTIVITIES

[75] Inventors: Paul J. Lawrence, Campbell; Terrence J. Andreasen, San Jose; David R. Shockey, Cupertino, all of Calif.

[73] Assignee: Litmus Concepts, Inc., Santa Clara, Calif.

[*] Notice: The portion of the term of this patent subsequent to Mar. 25, 2012, has been disclaimed.

[21] Appl. No.: 374,487

[22] Filed: Jan. 17, 1995

Related U.S. Application Data

[63] Continuation-in-part of Ser. No. 335,007, Nov. 7, 1994, abandoned.
[51] Int. Cl.⁶ .............................. C12Q 1/34; C12N 11/08; G01N 21/00
[52] U.S. Cl. ................................. 435/18; 435/24; 435/34; 435/805; 435/810; 422/61
[58] Field of Search ............................... 435/18, 24, 805, 435/810, 34; 422/61

[56] References Cited

U.S. PATENT DOCUMENTS 5,268,146  12/1993  Lawrence et al. .
5,416,003   5/1995  Lawrence et al. ........................ 435/18

FOREIGN PATENT DOCUMENTS

A0254000   1/1988  European Pat. Off. .
A0475045   3/1992  European Pat. Off. .
A0571939  12/1993  European Pat. Off. .
A8907152   8/1989  WIPO .
A9424306  10/1994  WIPO .

OTHER PUBLICATIONS

Thomas E. Barman, *Enzyme Handbook* (1969) vol. 1 Berlin: Springer–Verlag 2–3, 16–20.
Borivoj Keil, *Specificity of Proteolysis* (1992) New York: Springer–Verlag 3–4.
J. L. Thomason et al., *Proline Aminopeptidase Activity as a Rapid Diagnostic Test to Confirm Bacterial Vaginosis* (Apr. 1988) 71(4) Obstet. & Gynecol. 607–611.
Ronald R. Watson et al.,*Substrate Specificities of Aminopeptidases: A Specific Method for Microbial Differentiation* 1–14.
Judith Schoolmaker et al., *A New Proline aminopeptidase assay for diagnosis of bacterial vagionosis* 165(3) Am. J. Obstet. Gynecol. 737–741.
Janine A. James et al., *Is Trichomoniasis Often Associated with Bacterial Vaginosis in Pregnant Adolescents?* (Mar. 1992) 166(3) Am. J. Obstet. Gynecol. 859–863.
Charles H. Livengood III et al., *Bacterial Vaginosis: Diagnostic and Pathogenetic Findings During Topical Clindamycin Therapy* (Aug. 1990) Am. J. Obstet. Gynecol. 515–520.
Manoj K. Biswas, *Bacterial Vaginosis* (Mar. 1993) 36(1) Clin. Obstet. and Gynecol. 166–176.
J. L. Thomas N et al., *Quality Control Standards for the Proline Aminopeptidase Assay Used to Detect Bacterial Vaginosis* 160(3) Am. J. Obstet. Gynecol. 757–758.
Jessica L. Thomason et al., *Terconazole for the Treatment of Vulvovaginal Candidiasis* (Nov. 1990) 35(11) The Journal of Reproductive Medicine 992–994.
Sales Literature on Rap NH System for the Biochemical Identification of the Family Neisseriaceae, the Genus *Haemopphilus*, and Other Bacteria.
Sales Literature on Rap NH System for the Biochemical Identification of Medically Important Anaerobic Bacteria.

Primary Examiner—Carolyn Paden
Attorney, Agent, or Firm—Townsend and Townsend and Crew

[57]  ABSTRACT

The presence of an enzymatically active hydrolase in a fluid sample is detected by contacting the sample with a solid-phase conjugate which is susceptible to cleavage by the hydrolase, and simultaneously or shortly thereafter, contacting the sample with an indicator which undergoes a detectable change upon the action of a reporter group. The reporter group is part of the conjugate and is liberated from it either partly or entirely by the action of the hydrolase. The indicator is susceptible to action by the reporter group only upon decoupling of the reporter group from the remainder of the conjugate, the decoupling occurring either in part or entirely upon action of the hydrolase. Also provided by this invention are various forms of a dry, self-contained test device which contains the conjugate described above plus the indicator and all other reagents and components necessary to achieve a detectable indication of the presence or absence of a catalytically active hydrolase. Preferred embodiments of the device also contain positive and negative controls.

48 Claims, 5 Drawing Sheets

2

ASSAY FOR PROLINE IMINOPEPTIDASE AND OTHER HYDROLYTIC ACTIVITIES

CROSS REFERENCE TO RELATED APPLICATION

This application is a continuation-in-part of applicants' application Ser. No. 08/335,007, filed Nov. 7, 1994, now abandoned.

FIELD OF THE INVENTION

The present invention relates generally to assays for hydrolase activity (e.g., naturally occurring or artificially produced hydrolytic catalysts) in a sample or specimen. The present invention finds particularly useful application in the detection of bacterial vaginosis by assaying for the presence of proline iminopeptidase (alternatively, aminopeptidase) activity in a vaginal fluid sample.

BACKGROUND OF THE INVENTION

One of the most frequent reasons adult women seek medical treatment is for abnormal vaginal discharge and related symptoms. In women who visit their physician with a vaginal complaint, approximately 40% are diagnosed as having some form of vaginitis, and 90% of these cases are either: bacterial vaginosis (BV), trichomoniasis or vulvovaginal candidiasis. The most common among these is bacterial vaginosis. BV is associated with placental infection, premature delivery and low birth weight babies, increased septicemia, premature membrane rupture and episiotomy infection. As such, the need for rapid, accurate, cost-effective and simple point-of-care diagnostic tests for the detection of BV is of utmost importance.

The term "non-specific vaginitis" was the term initially used to distinguish this syndrome from the specific vaginitides caused by *Trichomonas vaginalis* and yeast (i.e., Candida species). Prior to 1955, the causes of non-specific vaginitis were through to be a wide variety of aerobic bacteria. In 1955, it was reported that *Haemophilus vaginalis* was the cause of this disease (Gardner and Dukes, *Am. J. Obstet. Gynecol.*, 69:962 (1955)). Subsequently, it was found that the specific organism had no absolute requirement for hemin and, thus, the name was changed to *Corynebacterium vaginalis*.

Also in 1955, a study was published by Gardner and Dukes which suggested that *Gardnerella vaginalis* was the causative agent of BV and, thus, the organism thought to be responsible for BV was renamed *Gardnerella vaginalis*. This theory was, however, discredited by subsequent studies revealing that this microbe, i.e., *G. vaginalis*, is present in the vaginal secretions of 40–50% of normal women, i.e., BV-negative women, and in those cured of BV (Dunkelberg, et al., *Obstet. Gynecol.*, 20:629 (1962)). As such, the considerable overlap in the levels of *G. vaginalis* found in BV-positive and BV-negative women has rendered the *G. vaginalis* cell level inconclusive evidence of the disease state (Amsel, et al., *Am. J. Med.*, 74:14 (1983).)

Since then, it has become apparent that, unlike other common infectious diseases, BV cannot be attributed to one specific etiologic agent, but instead results from the drastic alteration of the vaginal flora. The normally present aerobic Lactobacilli (i.e., the normal flora) become greatly reduced in number and there is a concomitant overgrowth of several anaerobic bacteria and other microorganisms, including *G. vaginalis*. This alteration in vaginal flora is accompanied by an increase in vaginal pH. In response to these findings, the term BV was introduced to describe this symptomatology, i.e., to describe increased vaginal discharge without signs of clinical inflammation resulting from a complex change in vaginal bacterial flora.

Although BV is the most common form of vaginitis, it is the most benign in symptomatology. The primary signs and symptoms of BV are increased vaginal discharge, genital malodor, increased pH and the presence of clue cells. Normal vaginal discharge is white and floccular, with a high viscosity. With BV, the discharge is non-adherent, clear, thin, white or yellow grey, homogeneous, non-viscous, and watery. Moreover, vaginal discharge from women with BV or trichomoniasis liberates a fishy, amine-odor when the vaginal fluid is mixed with 10% potassium hydroxide (KOH). No such odor is liberated with normal vaginal discharge or, with vaginal discharge from women with vulvovaginal candidiasis. In addition, the vaginal pH of women with BV or trichomoniasis is above 4.5, whereas the normal vaginal pH is less than 4.5. Finally, BV is often associated with the presence of "clue cells," i.e., vaginal epithelial cells to which a large number of bacteria (e.g., *G. vaginalis*, Mobiluncus species, etc.) are attached rendering the entire cell border obscure.

As such, the clinical "gold standard" method of diagnosing BV involves the examination of the following four vaginal fluid criteria: the presence of clue cells (greater than 20%); vaginal secretions which are white or gray, homogenous and with low viscosity; a vaginal fluid pH greater than 4.5; and fishy or fish-like amine-odor when the vaginal fluid is mixed with 10% KOH. While these tests require relatively inexpensive components to perform, they are not routinely employed in a clinical setting. Such tests are cumbersome, inconvenient, labor intensive, and time-consuming. More importantly, these tests are somewhat subjective and require the health care professional to have considerable expertise with the microscope, a tool not always available in clinics or offices.

In addition to the gold standard criteria, BV is sometimes diagnosed by assessing the shift in vaginal flora by examining Gram stained vaginal smears. This method, however, is difficult to perform and requires special training, thereby making it unsuitable for use in clinic or office settings. Alternatively, a sample of vaginal secretions can be sent to a laboratory for gas-liquid chromatographic analysis for the presence of short chain fatty acids and amines. Unfortunately, however, gas-liquid chromatography is time-consuming and expensive to perform.

In 1988, a report by Thomason, et al. (*Obstet. Gynecol.*, 71(4):607 (1988)) suggested that bacterial enzyme activity, specifically proline iminopeptidase activity, in vaginal fluid may be a suitable marker for BV. Thomason, et al. described a colorimetric assay for proline iminopeptidase activity requiring saline extraction of vaginal fluid from a clinical swab, centrifugation, and a four hour incubation at elevated temperature (37° C.). The enzyme catalyzes the following reaction:

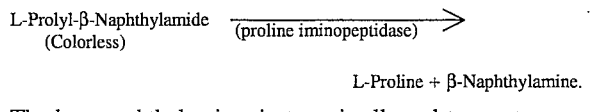

L-Prolyl-β-Naphthylamide (Colorless) →(proline iminopeptidase)→ L-Proline + β-Naphthylamine.

The beta-naphthylamine, in turn, is allowed to react spontaneously with a solution of a yellow dye, Fast Garnet GBC, for 5 minutes to produce a red color:

Unfortunately, the proline iminopeptidase assay system described by Thomason, et al., supra, requires four steps to perform. The first step involves the collection of vaginal fluid specimens on standard clinical swabs, and the freezing of the specimens until a sufficient number are available to test concurrently. As the second step, the swabs are thawed, the vaginal fluid is eluted from the swabs with saline, and the extracts are centrifuged to concentrate the insoluble, particulate matter into a pellet. If proline iminopeptidase activity is present in the specimen, it will be present in the particulate matter. As the third step, the pellet is resuspended in Tris buffered saline at pH 7.0 containing L-prolyl-β-naphthylamide and incubated for four hours at elevated temperature (37° C.). During this incubation period, the substrate will hydrolyze to release β-naphthylamine if proline iminopeptidase activity is present in the sample. As the fourth step, a freshly prepared solution of Fast Garnet is added to the suspension, and the mixture incubated for five minutes. If β-naphthylamine has been released by proline iminopeptidase or any enzyme having proline iminopeptidase activity, a red color is formed. In the absence of proline iminopeptidase activity, only the yellow color of the unreacted Fast Garnet chromogen is seen. The resulting assay as a whole is cumbersome, labor intensive, time-consuming and not suitable for use in a clinic or office.

The association of vaginal fluid proline iminopeptidase activity with BV has also been documented by Livengood, et al. (*Am. J. Obstet. Gynecol,* 163:515 (1990)) using an assay similar to that used by Thomason, et al., supra. Another study by Schoonmaker, et al. (*J. Obstet. Gynecol.,* 165:737 (1991)) utilized a different chromogenic substrate (i.e., L-prolyl-para-nitroanilide) to detect proline iminopeptidase activity in the vaginal fluid from women with BV and normal control women. In this study, the procedure described by Thomason, et al., supra. was performed concurrently on the specimens for purposes of comparison. The results obtained with the second chromogenic substrate produced diagnostic efficiencies (i.e., sensitivity, specificity, positive predictive value and negative predictive value) very similar to those seen in the Thomason study, supra.

The Schoonmaker, et al. procedure requires the following steps: (1) elution of vaginal fluid from clinical swabs and freezing the eluates at −70° C. until the tests were performed; (2) thawing the specimens and concentrating the particulate material by centrifugation; (3) resuspending the pelleted materials and pipetting aliquots into mitrotiter wells; (4) adding the chromogenic substrate to the microtiter wells and incubating the mixture at 37° C. for 4 hours; and (5) determining the presence or absence of a yellow color visually. Thus, as with the Thomason, et al. procedure, the Schoonmaker, et al. procedure is cumbersome, labor intensive, time-consuming and not suitable for use in a clinical or office setting.

In contrast to the foregoing, the ideal BV test for point-of-care use would have the following attributes: (1) room temperature stability to permit convenient storage in patient examining rooms; (2) the ability to use unprocessed or minimally processed vaginal fluid taken directly from the clinical swab; (3) rapid test results, immediately available to guide therapy or monitor therapy; (4) simple, specimen activated format and interpretation without multiple steps or components—ideally, the user would only be required to touch the unprocessed swab to the test system and check for color formation; (5) accuracy equal to that seen with clinical laboratory systems; and (6) built-in, specimen-activated positive and negative control elements to assure proper test performance.

To date, however, no convenient, simple, point-of-care assay has been developed for detecting the presence of enzymatically active proline iminopeptidase, or of any enzyme having proline iminopeptidase activity, in an unprocessed or minimally processed vaginal fluid specimen. Accordingly, the present invention overcomes the problems and disadvantages of the prior art and which has the attributes set forth above for the ideal BV test. Further, the methods and test devices of the present invention are also useful for assaying for the presence of other known hydrolases and hydrolase inhibitors present in unprocessed or minimally processed samples or specimens.

SUMMARY OF THE INVENTION

It has now been discovered that enzymatically active proline iminopeptidase (alternatively, proline aminopeptidase), other enzymes exhibiting proline iminopeptidase activity, and enzymatically active hydrolases in general, which are present in unprocessed or minimally processed vaginal fluid or any other liquid sample, can be detected in a rapid, simple and accurate manner. For proline iminopeptidase activity, the assay is useful for point-of-care detection and diagnosis of bacterial vaginosis. Likewise for other hydrolases, the assay provides detection and diagnosis of conditions and diseases associated with those hydrolases. The procedure is also useful as an assay for inhibitors of hydrolases, thereby serving as a means for the detection and diagnosis of conditions and diseases associated with abnormalities in the inhibitor levels.

The assay is performed by contacting the sample with a solid-phase conjugate which is susceptible to cleavage by the hydrolase, and either during or subsequent thereto, contacting the sample with an indicator which undergoes a detectable change upon the action of a reporter group which is a portion of the conjugate and is liberated from it either partly or entirely by the action of the hydrolase. Furthermore, the indicator is susceptible to action by the reporter group only upon decoupling of the reporter group from the remainder of the conjugate, the decoupling resulting either in part or entirely from the hydrolase.

Prior to decoupling, the reporter group and the indicator are precluded from interaction. This is due either to a chemical neutralization of the reporter group by the coupling, or of a spatial separation between the solid-phase conjugate and the indicator. Decoupling may therefore either (a) de-neutralize a neutralized reporter group which is already in contact with the indicator, or (b) release an active reporter group and either (i) permit the released reporter group to diffuse through the sample toward the spatially separated indicator, or (ii) be carried to the indicator by a sample-saturated swab or other sample-absorptive device. When a swab or sample-absorptive device is used, the conjugate itself may dissolve in the sample and be carried by the swab to the indicator, with hydrolysis occurring on the conjugate in the swab and continuing after the swab has contacted the indicator. Alternatively, the portion of the conjugate which remains after the hydrolysis may be insoluble in the sample, such that hydrolysis occurs only at the location of the conjugate, and only the released reporter group is picked up by the swab and carried to the indicator. Activation of the reporter group can also result from a sequential decoupling of the conjugate at different sites on the conjugate molecule, the analyte hydrolase being responsible for one of the decoupling reactions.

In samples which do not contain the hydrolase, therefore, or samples which do contain the hydrolase but also contain a hydrolase inhibitor, the reporter group is prevented from interaction with the indicator, whereas in samples which contain the uninhibited hydrolase, the interaction occurs and a change is detectable in the indicator. The invention is applicable to a wide range of hydrolases and hydrolase inhibitors.

Likewise, the invention lends itself to, and thereby encompasses, a wide range of geometries and spatial arrangements of the conjugate and the indicator. Both may be initially present on a common solid support or a solid support of unitary construction, or they may be on separate solid supports. The conjugate and the indicator may occupy a common region on a single support (particularly in cases where the coupling of the reporter group to the conjugate neutralizes the reporter group), or they may be spatially separated by an air gap within the support, by the free-standing solid support itself where the support is made of a porous material, or by localization in discrete regions on a common surface of a single support (the latter three in cases where the indicator change relies on diffusion or transport of the reporter group). Other possibilities will be readily apparent to the skilled clinician or manufacturer of laboratory test devices.

In certain embodiments of the invention, the conjugate and indicator are layered or impregnated in solid form on the surface or within the body of a solid support yet readily soluble in aqueous media. In these embodiments, the conjugate and indicator dissolve or disperse in the sample regardless of the presence or absence of the analyte in the sample. The analyte nevertheless causes activation of the reporter group, and the detectable signal arises from the indicator only when the analyte is present. In other embodiments, the conjugate, indicator or both are immobilized on the surface or within the body of the solid support, and remain so upon contact with the sample. The presence of the analyte then results in either activation or release of the reporter group into the sample where it can interact with, or through which it can travel to, the indicator.

The present invention further resides in dry, self-contained test devices useful for the assays described above. In one embodiment, the test device is comprised of layered, and possibly laminated, sheets which form an interior void space to receive and contain the sample, an opening through which the sample is admitted into the void space, and reagents deposited on, or otherwise applied to, one or more of the interior walls of the void space, the reagents including the conjugate and indicator described above, with the indicator visible from the exterior of the device through a light-transmitting wall. As in the method described above, these characteristics of the test device lend themselves to a wide variety of configurations, materials and designs, varying with the methodology of the assay and the manner in which the device is handled.

In another embodiment, the test device is comprised of the conjugate and indicator as solid-phase reagents in distinct layers or laminae separated by a intermediate fluid-penetrable layer. In still another embodiment, the test device is comprised of the conjugate and indicator as solid-phase reagents localized in discrete regions on the surface of a test device to permit the operator to obtain a reading by drawing across the surface a swab or other sample-absorptive device saturated with the sample.

These and other features, objects and advantages of the invention in all of its various aspects, including its preferred embodiments, will become apparent from the description which follows.

DETAILED DESCRIPTION OF THE INVENTION AND PREFERRED EMBODIMENTS

A. METHODOLOGY

Figure 1:
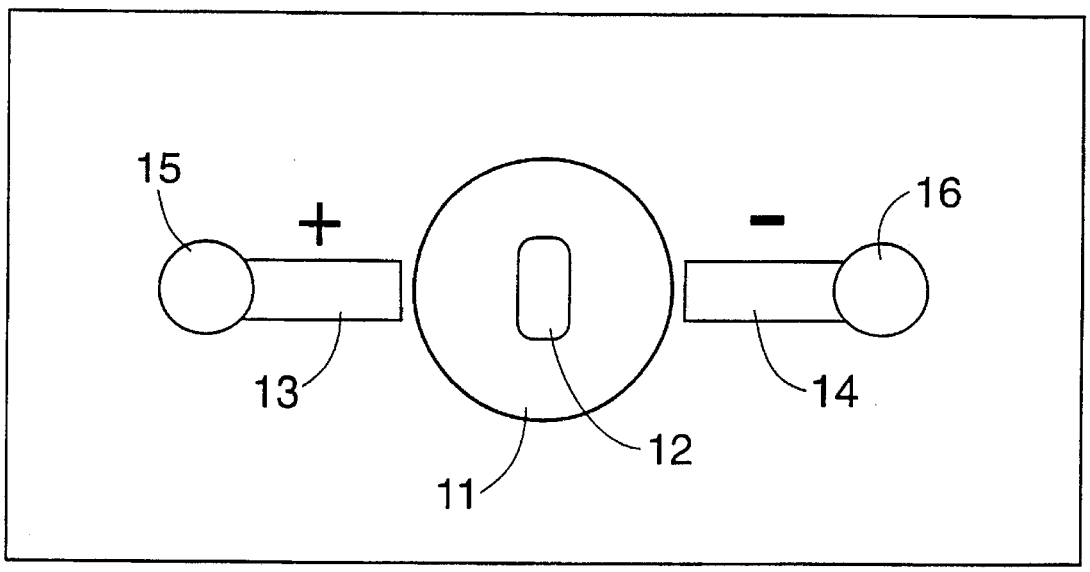
FIG. 1 is a top view of a one type of test device in accordance with the present invention.

The present invention is applicable to a wide variety of hydrolases and hydrolase inhibitors. The term "hydrolase" is used herein to refer to an enzyme or other natural or artificially produced entity which catalyzes hydrolytic reactions. More specifically, the term "hydrolase" is used herein to a catalyst that is capable of splitting a compound into fragments through the addition of water. In this reaction, the hydroxyl group of a water molecule is incorporated into one fragment, while the hydrogen atom is incorporated into the other fragment. Types of hydrolases susceptible to assay by the present invention include, but are not limited to, the following: hydrolases acting on ester bonds, hydrolases acting on glycoside bonds, hydrolases acting on ether bonds, hydrolases acting on peptide bonds, hydrolases acting on carbon—nitrogen (C—N) bonds other than peptide bonds, hydrolases acting on carbon—carbon (C—C) bonds, hydrolases acting acid-anhydride bonds, hydrolases acting on halide bonds, hydrolases acting on phosphorous—nitrogen (P—N) bonds. Hydrolases of particular interest in connection with this invention are those which act on peptide bonds. These hydrolases include, but are not limited to, the following: alpha-amino-acyl-peptide hydrolases, peptidyl-amino-acid hydrolases, dipeptide hydrolases, and peptidyl-peptide hydrolases. In a particularly preferred embodiment, the invention is applicable to assays for proline iminopeptidase, which is also referred to in the art as proline aminopeptidase, or any enzyme which exhibits proline iminopeptidase activity.

The term "conjugate" is used herein to refer to a reporter group coupled to a substrate residue yet capable of cleavage or decoupling therefrom upon contact with the catalytically active hydrolase whose presence is being detected. The term "reporter group" or (interchangeably) "marker group" is used herein to refer to a moiety which can be hydrolytically released from the substrate residue by a hydrolase and which, in its free form, can react with an indicator to produce a detectable change. Such reporter groups include, but are not limited to, the following: phenols, naphthols, aromatic amines, amino acids, their derivatives and analogs. In a particularly preferred embodiment, naphthylamine, its derivatives or analogs are used as the reporter group.

The term "substrate residue" is used herein to refer to a molecule or a portion of a molecule which is covalently coupled to a reporter group by means of a bond which is hydrolyzable by the hydrolase being detected. The reporter group when coupled to the substrate residue is incapable of interacting with the indicator, yet becomes capable of the interaction upon decoupling by hydrolysis. As mentioned above, the inability of the reporter group to interact with the indicator may be due either to a chemical neutralizing effect of the substrate residue or to a spatial separation between the conjugate and the indicator, or both. In any event, the bond between the reporter group and the substrate residue is one which is hydrolyzable either by the analyte hydrolase alone, by the analyte hydrolase acting in combination with other hydrolases, or by one or more hydrolases when not inhibited by an analyte inhibitor. The substrate residue is not itself a chromogen, stain or dye, either before or after enzymatic hydrolysis.

The substrate residue will be selected as one which when coupled to the reporter group is susceptible to action by the hydrolase of interest. Since hydrolases are frequently named according to the substrate which they hydrolyze, the selection of a substrate can often be readily made on this basis. For example, peptidases hydrolyze peptide bonds or amide analogs thereof; proline iminopeptidase hydrolyzes peptide or amide bonds in which the N-terminal amino acid is L-proline and its analogs or derivatives; glycosidases hydrolyze glycoside bonds; esterases hydrolyze ester bonds; acid phosphatases hydrolyze phosphate esters at low reaction pH; and so forth. The reporter group is coupled to the substrate residue using conventional methods and procedures. Suitable substrate residues for use in accordance with the present invention include, but are not limited to, amino acids, peptides, monosaccharides, disaccharides, nucleotides, carboxylic acids, alcohols, their derivatives and analogs. In one presently preferred embodiment, the substrate residue used is L-proline or hydroxy-L-proline.

Examples of conjugates are free or modified amino acid derivatives of phenols, naphthols, aromatic amines and amino acids. Such conjugates include, for example, amino acid-naphthylamides and structurally related amino acid and peptide analogs. In certain preferred embodiments, L-prolyl-beta-naphthylamide, L-prolyl-beta-methoxy-naphthylamide, or hydroxy-L-prolyl-beta-naphthylamide is the conjugate used for the detection of proline iminopeptidase activity.

The coupling of the reporter group to the substrate precludes interaction of the reporter group with the indicator, whereas decoupling due to hydrolysis permits the interaction to occur. An example of how this is achieved is by use of a substrate residue which is an oligopeptide, polypeptide, sugar, oligosaccharide, or other hydrolyzable entity which is schematically designated "A.B.C.D.E.", and the reporter group is covalently bonded to the E segment of the residue to form the conjugate, which can then be represented as "A.B.C.D.E-reporter group". The "E" segment in this example acts as a neutralizing agent to the reporter group, and the substrate residue is initially either covalently bonded to the solid support or is simply adhered to it in such a manner that it dissolves in the sample upon contact. If the hydrolase specifically hydrolyzes the bond between E of the substrate residue and the reporter group, the neutralizing effect of E is terminated and the reporter group is activated and released in free form into the sample. If the remainder of the residue is also released into the sample, the sample will contain both a non-signal generating substrate residue (i.e., A.B.C.D.E) and a free reporter group which can in turn react with the indicator to produce a detectable change.

If however the hydrolase of interest hydrolyzes the conjugate at the bond between A and B, or at any other point other than between E and the reporter group, the hydrolase by itself would be incapable of releasing the reporter group in active form. One or more assisting hydrolases which could only act in conjunction with the hydrolase of interest could then be incorporated into the assay to complete the release of the reporter group in active form. The assisting hydrolase or hydrolases must therefore be ones which are incapable of releasing the reporter group directly from the intact conjugate, but instead capable of releasing the reporter group only from the cleavage product generated by the hydrolase of interest.

An example is shown schematically hereinbelow.

First, the hydrolase of interest, unable to release the reporter group directly, specifically hydrolyzes one or more bonds in the conjugate, thereby releasing a molecular fragment containing the inactive reporter group:

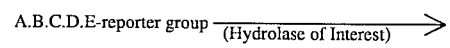

A.B.C + D.E-reporter group.

Next, the assisting hydrolase (or hydrolases) releases the reporter group by hydrolyzing the bond between E of the substrate residue fragment and the reporter group in one or more steps:

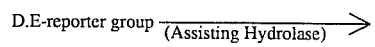

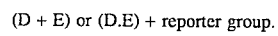

(D + E) or (D.E) + reporter group.

The net effect of the foregoing reaction sequence is the release of the reporter group only when the hydrolase of interest is present in the sample. As such, the reporter group can be released from the substrate residue by the hydrolase acting alone or, by the hydrolase acting in combination with an assisting hydrolase or hydrolases. The selection of appropriate assisting hydrolases will depend on the substrate residue bound to the reporter group and will be readily apparent to those skilled in the art.

The term "indicator" is used herein to refer to any species which undergoes a detectable change as the result of the reaction or, as a result of the culmination of the reactions occurring when the catalytically active hydrolase is present in the sample or specimen. The resulting detectable change is an indication that the reporter group was released from the substrate residue and, thus, that the catalytically active hydrolase being assayed for is present in the sample. Moreover, the indicator is preferably of a composition which is substantially insoluble in the sample so that the indicator is immobilized on the solid support, i.e., so that the indicator remains predominantly on the solid support throughout the duration of the assay. For samples in either aqueous or water-soluble media, therefore, the preferred indicator is either an indicator which is substantially insoluble in water or, an indicator held in a matrix which is substantially insoluble in water.

Preferred indicators are visual indicators and, in particular, chromogenic indicators, i.e., those in which the visible change is a change in color, including the formation of color in an otherwise colorless material, upon action of the reporter group when it is released from the substrate residue by the catalytically active hydrolase whose presence is being detected. Alternatively, the reporter group may be capable of interacting with an indicator to generate a fluorescent signal, a phosphorescent signal, a bioluminescent signal, a chemiluminescent signal or an electrochemical signal upon its release from the solid support by the action of the hydrolase.

In these cases, the indicator would be the chemical species required by the reporter group in order to bring about the desired detectable change.

A wide variety of chromogenic indicators (i.e., chromogens) and other species having a similar effect may be used as visual indicators when phenols, naphthols, aromatic amines, amino acids, their derivative and analogs are used as the reporter group. In accordance with the methods of the present invention, preferred chromogenic indicators include, but are not limited to, diazonium salts and tetrazonium salts. In a presently preferred embodiment, the chromogenic indicator is a diazonium salt. Suitable diazonium salts include, but are not limited to, the following: Fast Garnet GBC, Fast Dark Blue G, Fast Red B, Fast Corinth V, Fast Bordeaux and Fast Black K, all of which are colorless or lightly colored in their unreacted state, but which form highly colored derivatives with reporter groups consisting of phenols, naphthols, aromatic amines or their structural analogs. See, H. J. Conn's "Biological Stains" (R. D. Lillie, M.D. (ed.), Baltimore: The Williams & Wilkins Co., ninth edition (1977), pp. 200–224), the teachings of which are incorporated herein by reference, for a detailed review of suitable diazonium and tetrazonium salts which can be used as indicators when phenols, naphthols or aromatic amines are used as the reporter group.

In addition, numerous chromogenic indicators for reporter groups consisting of amino acids are also known to those skilled in the art. An example of a suitable chromogenic system which can be used when the reporter group is an amino acid comprises: an amino acid oxidase; a chromogen selected from the group consisting of guaiac, 2,2'-azino-bis(3-ethyl-benzthiazoline-6-sulfonic acid), tetramethylbenzidine, phenol, 4-aminoantipyrine and 4,5-dihydroxynaphthalene; a redox catalyst selected from the group consisting of peroxidases, iron protoporphyrin and metal ions; and oxygen. It will be readily apparent to those in the art that amino acid oxidases can use oxygen from the air. An example of this type of chromogenic indicator system is shown schematically hereinbelow:

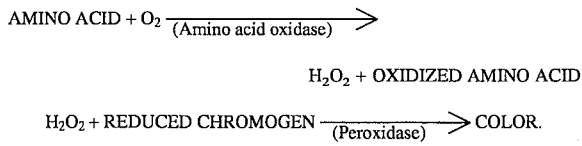

As such, the most appropriate chromogenic indicator for any given reporter group will depend on the substrate specificity of the hydrolase, the actual reporter group employed and the reaction conditions needed for a given test. The selection in any given case will be readily apparent to those skilled in the art.

Any of a wide variety of materials can be used as the solid support. Note that the term "solid support" is used herein to denote the free-standing backing material to which lamina are applied, as opposed to any of the lamina themselves. Examples of materials suitable for the solid support are insoluble polymeric materials, inorganic or organic matrices, gels, aggregates, precipitates and resins. Solid supports in accordance with the present invention include, but are not limited to, the following: cellulose, agarose, dextran, polyacrylate, or their derivatives, starch, polyacrylamide, nylon, polyethylene terephthalates, polyethylenes, polystyrenes, polypropylenes, polycarbonates and glass. In certain preferred embodiments, Mylar® and Mylar®/polyethylene laminates are used as the solid support.

The solid-phase reagents of the invention are retained or deposited on the solid support in a manner which may or may not cause them to remain in place on the support surface even upon contact with the sample rather than diffusing or dissolving in the sample. The term "immobilized" is used herein to refer to the affixation or adherence of the component in question to the solid support in such a manner that the component remains substantially affixed or adhered throughout the assay. Immobilization may be achieved in any manner which maintains the species in position on the support, and the term is used independently of the manner of applying the species to the support or the means of maintaining it in contact with the support. Chemical means of immobilization may be used as well as physical means. In the case of components which are deposited but not immobilized, the adherence may last only until the support is contacted with the liquid sample, i.e., the initially adhered component either dissolves or is readily dispersed in the liquid upon contact. Immobilized components, by contrast, are not released into the liquid by simple contact with the liquid. Solid-phase deposition in accordance with this invention, whether or not it involves immobilization, thus encompasses covalent bonding, specific and nonspecific binding affinities, impregnation and various forms of impermanent adherence. Examples of application methods are coating, spraying, printing, stamping, ink jet spraying, and dipping.

The solid-phase species will generally be restricted to a defined area on the surface of the support. Often, the area will constitute, or be part of, a geometric or iconic pattern with either a functional purpose, a decorative purpose, or both. When two or more solid-phase species are present, the pattern may serve to spatially separate one from the other, or to assist in differentiating the species from one other for the benefit of the user. The area for any given species may be continuous as in a filled circle, a ring, a cross, a strip or other such shape, or discontinuous as in an array of dots or stripes.

Indicators, for example, can be impregnated onto a bibulous paper or support or, deposited onto a plastic or other sheet in the form of a thin layer. The chromogen can be layered as a solution or suspension containing a film forming polymeric material (such as, for example, celluloses, polyacrylates and their derivatives).

Preferably, the indicator is immobilized on the solid support in a manner which renders it largely insoluble in the sample. If the indicator is a water soluble chromogen, it can be trapped in a matrix of material which is substantially insoluble in water. Alternatively, if the chromogen itself is insoluble in water, it can be layered as a suspension in water or as a solution in an organic solvent either alone or in combination with a water-soluble or water-insoluble film-forming polymer. In a presently preferred embodiment, water-insoluble ethylcelluloses are used as film-forming polymers.

The reagents of the assay may be arranged in a variety of ways on the test device. For example, the conjugate and the indicator may be on different lamina of a laminated device, separated only by an air gap to be filled by the test sample. Any reporter group released by enzymes in the test sample may then diffuse through the sample toward the indicator where it will induce the detectable change. Alternatively, the conjugate and indicator may be present on the same flat solid support, for example one on one of the faces of the support and one on the other face. The support can be porous (such as a woven or non-woven polymer) or solid with a series of very fine holes passing through it to permit saturation of the support with the sample and diffusion of the reporter group from one side to the other.

Alternatively, the conjugate and the indicator may be horizontally segregated on the same surface of a single solid support. With the conjugate is deposited on one portion of the surface and the indicator on another, the sample can be wiped or streaked across the surface from the conjugate to the indicator. As indicated above, the methodology for this type of device may vary. As one example, the conjugate itself may dissolve in the sample and be carried by the swab to the indicator, with hydrolysis of the conjugate occurring in the swab and continuing after the swab has contacted the indicator. As another example, the portion of the conjugate which remains after the hydrolysis may be insoluble in the sample, with hydrolysis occurring only at the location of the conjugate, and only the released reporter group being carried by the swab to the indicator. One example of a geometric arrangement for this implementation of the invention is a "bull's eye" or "target" pattern, in which the indicator occupies a filled circle while the conjugate is arranged in a ring surrounding but not contacting the circle. Other geometries will be readily apparent.

To illustrate an implementation of the present invention for detecting proline iminopeptidase activity, the sample is placed in a device which contains first and second solid supports, the first solid support being a Mylar® polyethylene laminate on which an L-prolyl-beta-naphthylamide, L-prolyl-beta-methoxynaphthylamide of hydroxy-L-prolyl-beta-naphthylamide conjugate is deposited, the second solid support being a Mylar® polyethylene laminate on which Fast Garnet GBC, a chromogenic indicator which undergoes a detectable change upon action of beta-naphthylamine, is deposited. The sample is placed in the device in such a manner that the sample contacts the first and second solid supports such that any beta-naphthylamine released by proline iminopeptidase activity in the sample is permitted to diffuse through the sample to the second solid support. The Fast Garnet GBC is then observed for a detectable change as an indication of the presence of the enzyme in the sample. The conjugate may be incorporated in a matrix of water-soluble polymer such as hydroxypropyl cellulose. The Fast Garnet GBC indicator may be incorporated in a water-insoluble matrix of ethylcellulose which contains a penetrant such as manganese chloride.

Reaction conditions can be selected, modified and regulated to increase hydrolase sensitivity and specificity, and to differentiate between different hydrolases in a sample. Examples of reaction conditions which can be controlled in this manner, aside from the choice of substrate residues, reporter groups, indicators, and solid supports, are pH, the inclusion and choice of buffer and buffer capacity, and the inclusion and choice of salts, detergents, metal ions, reducing agents, and chelators. For example, it is known that certain hydrolases function at a low pH and are inhibited at a high pH. Other hydrolases function at a high pH and are inhibited at a low pH. Thus, by regulating the pH of the assay, one will be able to selectively detect the presence of a particular hydrolase. Moreover, it will be readily apparent to the skilled artisan that one or more hydrolase inhibitors can also be used in the presently claimed methods to permit the activity of a given hydrolase to be detected, while inhibiting interfering hydrolases which may be present in the sample, thereby increasing the sensitivity and specificity of the assay for the hydrolase of interest.

The present invention can be used to assay simultaneously for the presence of two or more catalytically active hydrolases in a sample or specimen. This is achieved by using a combination of two or more reporter groups coupled to different substrate residues and deposited on one or more solid supports, each reporter group releasable from a given substrate residue by only one of the hydrolases potentially present in the specimen, each substrate residue employing a different reporter group, and two or more indicator systems, each capable of producing a detectable response with only one of the reporter groups. For example, with the present invention one can simultaneously detect a mixture of a glycosidase and a peptidase, thereby obtaining a hydrolytic profile of a given pathogen or disease process. In this assay, two different, specific substrate residues each of which inactivates a different, specific reporter group, and two different reporter group-specific indicators would be employed.

In its application to the detection of hydrolase inhibitors, the present invention extends to a wide range of analytes and samples. Many biological processes, including regulation of blood pressure, blood clotting, bacterial replication, etc., involve the use of very specific, carefully modulated hydrolases. Moreover, numerous drugs, pesticides, and herbicides, etc., are known to function by virtue of inhibiting specific hydrolases. Under certain circumstances, it is highly desirable to determine the blood, saliva or urine concentration of a hydrolase inhibiting therapeutic drug or to determine the presence of a potential pesticide hydrolase inhibitor contamination in produce, etc. The analyte in these cases is the inhibitor of a hydrolase rather than the hydrolase itself.

The need to analyze for the presence of an active hydrolase inhibitor arises in two circumstances—(1) when the target hydrolase of the inhibitor (i.e., the particular hydrolase that the inhibitor is known to inhibit or inactive) is present in the sample prior to the analysis, and (2) when the target hydrolase is not present in the sample and must be added to the test system. When the hydrolase is not present, a defined quantity of the hydrolase is incorporated into the test system, and the test performance involves detecting the ability of the sample to inhibit the target hydrolase. The hydrolase may, for example, be applied to one of the solid supports in the same manner as the conjugate, or the hydrolase may be added to the sample prior to contact of the sample with the test device.

In the event that the target hydrolase inhibitor is not present in the sample, the target hydrolase will release the reporter group from the substrate residue, thereby producing a detectable change in the indicator. Conversely, if the target hydrolase inhibitor is present in the sample, the target hydrolase will be inhibited, the reporter group will not be released from the substrate residue, and a detectable response will not be produced in the indicator. The particular target hydrolase used in the above method will depend upon the inhibitor which is being detected, and the selection in any given case will be readily apparent to those skilled in the art. It is not necessary that the inhibitor in the sample completely inhibit the target hydrolase added to the test system. All that is required is that a sufficient amount of target hydrolase inhibition occurs to produce a noticeable difference in the anticipated detectable response. Among the inhibitors which can be tested in this manner are inhibitors of any of the hydrolases mentioned above.

The present invention is useful in testing samples for the presence of a hydrolase from a wide range of sources, including biological sources and others. Examples of bodily fluids on which the assay can be performed are blood, serum, plasma, urine, urethral discharge, tears, vaginal fluid, cervical exudate, spinal fluid and saliva. Examples of non-bodily fluids are plants, foods, microbial cultures and liquid wastes.

A significant advantage of the present invention is that the sample does not have to be fully processed prior to assaying for the presence of a given hydrolase. For example, when vaginal fluid is assayed for the presence of proline iminopeptidase activity using methods of the prior art, the vaginal fluid must be diluted and centrifuged, and the particulate material itself diluted and resuspended, prior to the assay. These steps require special equipment, additional reaction components and extended incubation times at elevated temperatures. The present invention, in contrast, can be performed on unprocessed vaginal fluid (i.e., vaginal fluid which has not been diluted, centrifuged or otherwise manipulated) or, minimally processed vaginal fluid (vaginal fluid which has been diluted with, for example, saline). This advantage extends to other types of samples as well. The present invention can likewise be used with samples that have been fully processed, but such processing is optional. Thus, the present invention can effectively and efficiently performed on unprocessed, minimally processed or fully processed samples or specimens.

B. TEST DEVICES

The test device aspect of this invention resides in three basic test device constructions, each of which, with the appropriate selection and arrangement of materials and reagents, is suitable for performing the assays described above. The first of these constructions is a laminated panel with an internal void space or chamber and an opening or port leading into the chamber for insertion of the sample. The second construction is a free-standing panel of penetrable material which provides the panel with its rigidity, shape and structural integrity, with the reagents deposited in layers on opposing sides of the penetrable panel. The sample is applied to one of the layers and diffuses through the penetrable panel to the lay on the opposing side. The third construction is a panel with the reagents occupying discrete regions on a panel without the need for penetrating the panel. The sample is applied to one of the regions by an applicator, which is then applied to the other region. Both regions are preferably on the same side of the panel. In all three constructions, the reactive species are constituted and arranged such that the reactions which culminate in the detectable change in the indicator occur only when the sample has been applied. In the first construction, the application of the sample will result in the chamber being filled. In the second, the application of the sample will provide a liquid diffusion path through the panel. In the third, the sequential contact of the sample-wetted applicator will result in contact between the different reagents by means of the applicator.

These three constructions will now be described in detail.

1. Panel With Chamber

For convenience, the parts of the panel and the locations of the functional chemicals in the panel will be described from a frame of reference in which the panel is in a horizontal position, since this is the most likely position which the panel will occupy during use. With the panel in this position, particularly for thin, flat panels, the sample application port is preferably located in the top surface of the panel in the uppermost lamina. The ceiling or upper surface of the chamber is formed by the lower surface of the uppermost lamina. Likewise, the floor or lower surface of the chamber is the upper surface of the bottom or lowermost lamina. The thin edges along the perimeters of the panel form the side edges of the panel, and the thin lateral extremities of the chamber along the edges of its ceiling and floor form the side walls of the chamber. Regions of any given surface which are adjacent to each other in the same horizontal plane will be referred to as horizontally adjacent, whereas laminae positioned one directly over the other to form parallel horizontal planes will be referred to as vertically adjacent.

The top lamina, bottom lamina, or both are fabricated of a light-transmitting, preferably transparent, material. The conjugate, indicator and other components and reagents needed for the test are arranged in one or more laminae within the chamber, either as dry coatings on the upper surface of the chamber, the lower surface of the chamber, or both. As indicated above, dried conjugate, indicator or any other dried reagents can be physically separated by placement on different surfaces, by horizontal separation on the same surface, or by vertical separation on a single surface. For horizontal separation of reagents on a single surface, laminae can be deposited in geometric patterns which prevent their direct contact. Vertical separation can be achieved by the chamber itself or by the use of intervening laminae of polymeric films or other inert materials. The lamina containing the indicator may be on the ceiling or floor of the chamber. One or more of the reagents may be included in the same lamina as the indicator or, in separate, horizontally or vertically adjacent laminae on the same surface or on opposite surfaces. In certain preferred embodiments of the invention, the indicator is located directly underneath a light-transmitting wall forming the ceiling of the chamber, and the conjugate is located directly below on the floor of the chamber.

The chamber is preferably flat and shallow with a width and length much greater than its depth, the depth being substantially constant. The chamber is preferably shallow enough to promote spontaneous wetting of the chamber walls with the specimen to achieve the maximum contact between the specimen and the dry reagent coatings on the chamber surfaces. This is of particular interest when reagent coatings are present on both the upper and lower surfaces of the chamber. In such cases, a small constant distance between these surfaces will also minimize the distance over which the reagents on the surface opposite that to which the visual indicator has been applied will need to diffuse in order to reach the indicator.

The light-transmitting wall may be any material which is inert and sufficiently rigid to support the indicator lamina, and yet sufficiently transmissive of light to show the change in the indicator as seen as it occurs. Translucent or transparent materials, preferably nonabsorptive materials, may be used; transparent materials are preferred. Examples of transparent polymeric materials suitable for this use are polyethylene terephthalates (such as, for example, Mylar®) and polycarbonates (such as, for example, Lexan®). The opposing (i.e., bottom) wall of the device may likewise be made of transparent or translucent material, although it may also be of opaque material since visualization of the test results as well as the positive and negative controls is required only from one side of the device. When the bottom wall is transparent, detection of the change in the test area, control areas or both through the top wall can be enhanced by applying a printing or coating to ether surface of the bottom wall with a colored or reflective material to heighten the color contrast.

The sample introduction port is preferably in the same wall through which changes in the visual indicator are observed, i.e., the light-transmitting wall. The port will be shaped to accommodate the transfer device which is used to convey the sample from its source. The shape of the port may in fact be varied to suit any of the various types of transfer devices which might be used. Examples of transfer devices are syringes, pipets, swabs and specula. Others will readily occur to those skilled in the art. A circular port is generally adequate, although for transfer devices such as swabs, the port may contain a straight edge along which the transfer device can be scraped to more easily release the specimen.

Preferred embodiments of this type of test device contain additional features which further promote the fluid migration needed to fill the chamber and thereby place all reagents in contact with the specimen. One such feature is the inclusion of one or more vent holes in the chamber to permit the escape of air. The vent holes will be adequately distanced from the sample introduction port to maximize the surface area wetted by the specimen. In devices where specimen-activated positive and negative controls are included inside the chamber in positions horizontally adjacent to the test area or the sample port, the vent holes will be arranged to assure that the specimen reaches both controls and fills them to avoid any false or ambiguous readings. In one preferred arrangement, the test area or sample port is placed between the control areas such that the positive and negative control areas do not share a common boundary although each does share a common boundary with the test area or sample port. In this arrangement, the sample port is most conveniently placed at a location in the wall directly above or immediately adjacent to the test area, and one vent hole is placed above each of the two control areas at or near the outer extremities of these areas, thereby causing the specimen to fill first the test area around the sample port and then both control areas.

This test device may be formed in a variety of ways. Sheets of polymeric material may be laminated together, with appropriate cutouts in a central sheet to define the shape of the chamber and holes for the sample introduction port and the vent holes. The depth of the chamber as well as its shape and lateral dimensions will then be defined by the thickness of the central sheet and the size and shape of the cutouts, while the placement of the holes will be controlled by the top sheet. The indicator and reagent coatings may be applied to the top sheet, bottom sheet or both, as required, before the sheets are assembled into the laminate. The sheets may then be secured together by any conventional means, such as, for example, by heat sealing or through the use of adhesives.

A particularly preferred method of forming the device is by the use of a single sheet of transparent or otherwise light-transmitting polymeric material, with one or more sections of the sheet embossed or otherwise processed, mechanically or chemically, to contain one or more depressions or indentations of constant or variable depth in the inner surface of the chamber. A depression or can be located on one half of the sheet, with the holes for sample introduction and venting on the other half for sample introduction and venting in one or both depressions. Alternatively, for some applications, depressions can be located on both halves of the sheet, with holes for sample introduction and venting on only one half. The indicator and reagent coatings are applied at appropriate locations on the sheet, and the half containing the holes is then folded over the other half to form the enclosed chamber and to achieve correct alignment of the areas representing the upper and lower surfaces of the chamber. The facing surfaces of the sheet are bonded together as in the laminate of the preceding paragraph.

A preferred method for bonding the two halves together is through the use of a heat-sensitive, pressure-sensitive, water-based or solvent-based adhesive. The adhesive may be restricted to the areas peripheral to the chamber to avoid contact with the test reagents, or it may cover the entire surface of the sheet, having been applied prior to application of the indicator and reagent coatings. In the latter case, appropriate adhesives will be those which are transparent, inert, wettable by, and otherwise compatible with the layers to be applied over them. Many types of adhesives suitable for this application exist, and the most appropriate choice will vary from one system to the next depending on the layers to be applied above them.

Figure 2:
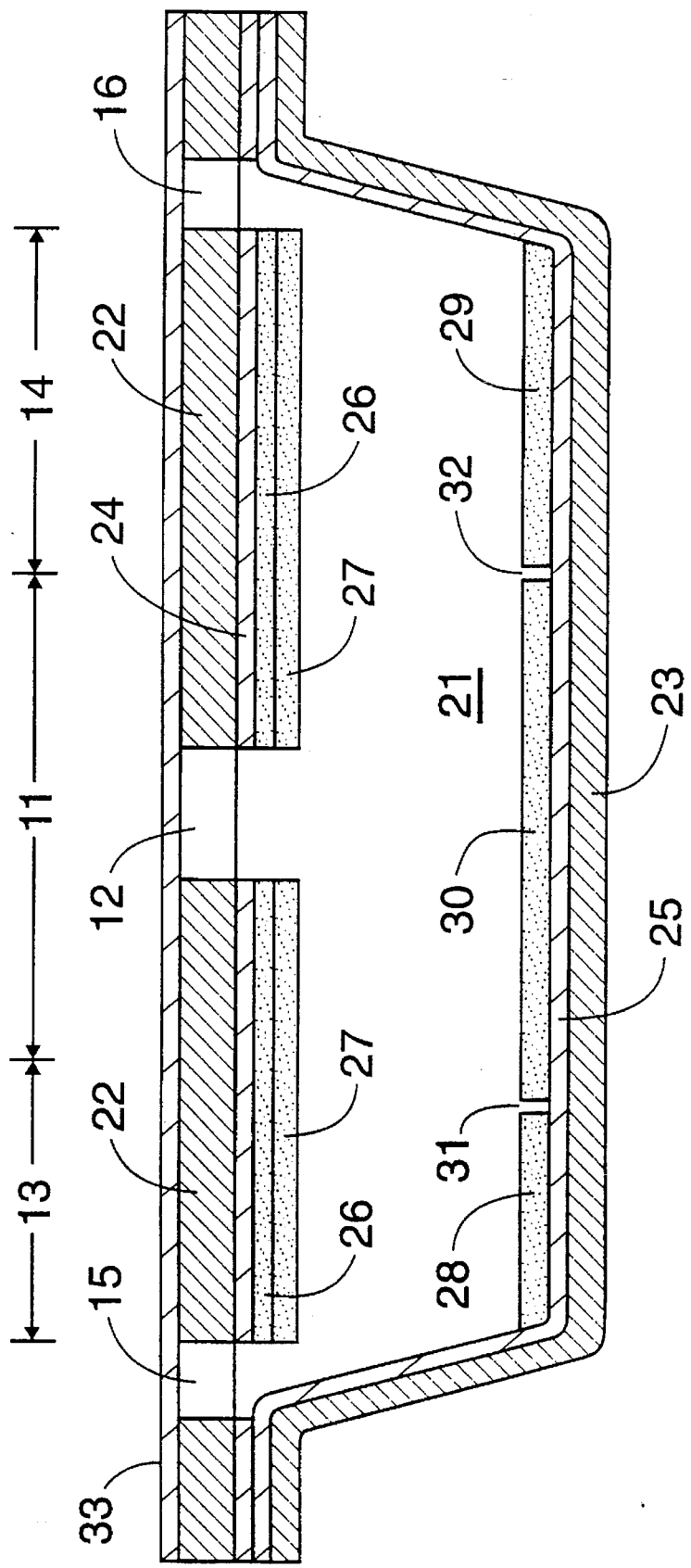
FIG. 2 is a side cutaway view of the test device of FIG. 1.

One example of a panel in accordance with this description is shown in FIGS. 1 and 2. The top view of FIG. 1 shows a central circular test area 11 with a sample introduction port 12 in the center of the test area. A positive control zone 13 is located to one side of the test area, and a negative control zone 14 to the other. At the extreme outer ends of each of these control zones are air vents 15, 16. The side cutaway view of FIG. 2 shows the chamber 21 formed between two structural sheets of solid material 22, 23, which are formed of a transparent polymer, conveniently made from a single sheet folded over. The inner surfaces of each of the upper and lower walls of the chamber are coated with layers of adhesive 24, 25. The upper wall also contains a layer of indicator 26 and a layer of reagent 27. These two layers extend the full length and width of the chamber, surrounding the sample introduction port 12. On the bottom wall of the chamber, a reagent for the positive control 28 is in alignment with the positive control zone 13, and a reagent for the negative control 29 is in alignment with the negative control zone 14. A test reagent 30 as needed to perform the test for the presence or absence of the hydrolase or its inhibitor occupies the region in alignment with the test area 11. The three reagents on the bottom wall are separated by gaps 31, 32 to prevent mutual diffusion which might obscure the observed result. Although not shown, gaps can also be present on the top wall. A peel-off protective sheet 33 covers the top surface of the panel.

2. Liquid-Penetrable Panel

In this construction, the panel itself is a free-standing, self-supporting card or sheet of porous material, preferably flat and thin, and the reagents are applied to opposite sides of the panel. To use the panel, the sample is applied to the reagent on one side and permitted to diffuse through the panel to the reagent on the other. Penetrable panels can be fabricated in a variety of ways. For example, bibulous materials like particles of cellulose or other organic or inorganic, natural or synthetic materials can be suspended in a liquid medium, forming a thin film of the suspended materials by filtration. When the residual liquid is removed by evaporation, the product is a porous film which can be separated from the receptable in which it was formed and used as a free-standing panel. Penetrable panels can also be constructed of woven or non-woven polymer fibers or threads, with or without additional binders.

Microporous membranes can also be used as penetrable panels. Microporous membranes are often fabricated by casting thin films of a polymer, like nitrocellulose, in a solvent mixture, and allowing differential evaporation of the solvent mixture to create defined pores or channels throughout the film. Pore size, number and density can be carefully controlled by proper formulation of the solvent system and, in addition, by controlling the evaporation temperature.

Penetrable panels can be made from a film-forming polymer by adding porous or non-porous solids to a solution or suspension of the polymer during the casting of a film. Solids which can be used in this manner include, but are not limited to, the following: diatomaceous earth, Fuller's earth, Kaolin, microporous glass beads, fumed silica, molecular sieves and numerous other materials which allow penetration of a liquid sample through the film. In some cases, a penetrable film-forming polymer can be made by incorporating specimen-soluble additives including, for example, salts, sugars, polymers or, other materials which are soluble in both the sample and the solvent mixture used to cast the polymeric film. When the sample is added to the film containing such additives, the soluble additive dissolved, thereby permitting passage of the sample through the film.

In addition, porous polymeric sheets can be fabricated from non-sample-permeable films, sheets or supports by mechanically or chemically generating holes or channels in the otherwise solid films, materials or supports. Lasers or nuclear particles, for example, can be used to create precisely defined pores in suitable polymeric sheets. Small holes, pores or channels can be created in otherwise solid materials by etching, punching, drilling, boring, puncturing, perforating, cutting or abrading. One can treat the entire film, sheet or support in this manner or, alternatively, treatment can be restricted to a small defined area where sample is to be applied.

In this type of test device, it may be desirable to prevent the reagents from migrating in the lateral or radial direction, i.e., parallel to the flat surfaces of the device, during the test. This can be achieved by a radial migration barrier. Such a barrier can be generated by depositing a solution or suspension of a sample-impermeable material on the upper and lower surfaces of the panel in a defined geometric or iconic pattern and in a manner which does not cover specific areas on the upper and lower surfaces of the panel. The solution or suspension is permitted to penetrate the thickness of the panel, and the solvent is removed by evaporation. To deposit the migration barrier solution or suspension in identical aligned patterned regions on both surfaces of the panel, it is only necessary that each application penetrate slightly more than half the thickness of the panel. In this manner, the solutions or suspensions will penetrate the complete thickness of the panel, rendering it impermeable except in the areas specifically left untreated. Due to the thinness of the panel, vertical penetration by the migration barrier suspension or solution is rapid, and lateral migration of such solution or suspension into untreated test zones is minimized, thereby allowing the geometric length and width of the untreated sample application and test interpretation zones to be precisely defined. The radial migration barrier leaves a vertical diffusion channel with well-defined dimensions. This channel minimizes the quantity of sample needed to produce a test result. The channel can also be used to achieve an iconic or geometric readout of the test result.

Radial migration barriers can be prepared from various materials and applied in various ways. For water-based samples, a water-insoluble barrier is preferred. Examples are organic solvent solutions or suspensions of paraffins, waxes, and oils, water-insoluble cellulose derivatives, polyacrylate polyester, and polyamide derivatives, water-insoluble adhesives, radiation curable polymeric compositions, and numerous other water-insoluble materials. A barrier of paraffin, for example, may be applied as a solution in toluene. A barrier of ethylcellulose may be applied as a solution in alcohol. Water-insoluble hot melt adhesives can also be used.

A solution of suspension of the barrier material can be applied onto each surface of the panel by printing, spraying, brush application, or any other kind of deposition. With an appropriate selection of solvent systems and control of the amount applied and of the temperature and air flow across the panel, the barrier material applied to both surfaces of the panel will penetrate the panel. The solvent can then be evaporated to result in barrier of defined shape enclosing a porous vertical channel whose lateral dimensions reflect the contours of the applied barrier. With the length, width and shape of the vertical channel thus defined, detectable changes in the indicator can be confined to a defined, geometric pattern.

The solution or suspension of barrier material can further include pigments, either dissolved or suspended, which permit visualization of the barrier, as well as differentiation among the sample application area(s) and the test and control interpretation zones. The migration barrier can also be formulated to permit further printing of instructions and other indicia on either or both surfaces of the support.

With a visible migration barrier in a geometric pattern, the reagent and indicator can be applied on the upper and lower surfaces of the support in complementary patterns defined by the barrier pattern. If the reagent is sample-soluble, the sample when applied to the reagent side of the support will dissolve the reagent and diffuse through the channel to the indicator. The reporter group carried by the sample then causes a detectable change in the indicator if the analyte of interest is present in the sample. The migration barrier directs essentially all of the sample and reagent toward the indicator, and consequently, the test result is readily detectable in a manner permitting geometric or iconic readout.

Figure 3A:
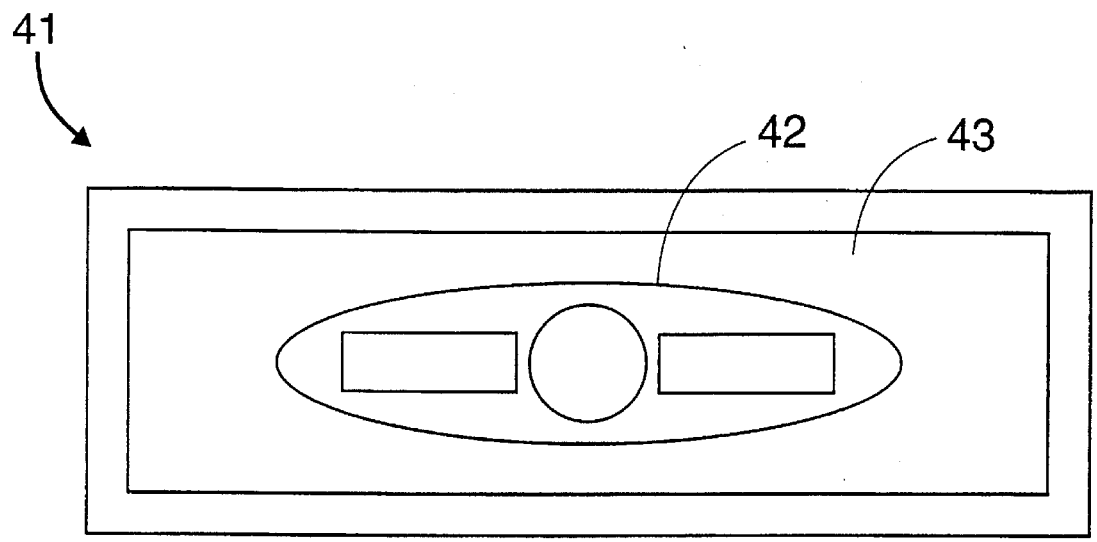
FIGS. 3a and 3b are top and bottom views of a second type of test device in accordance with the present invention.
Figure 3B:
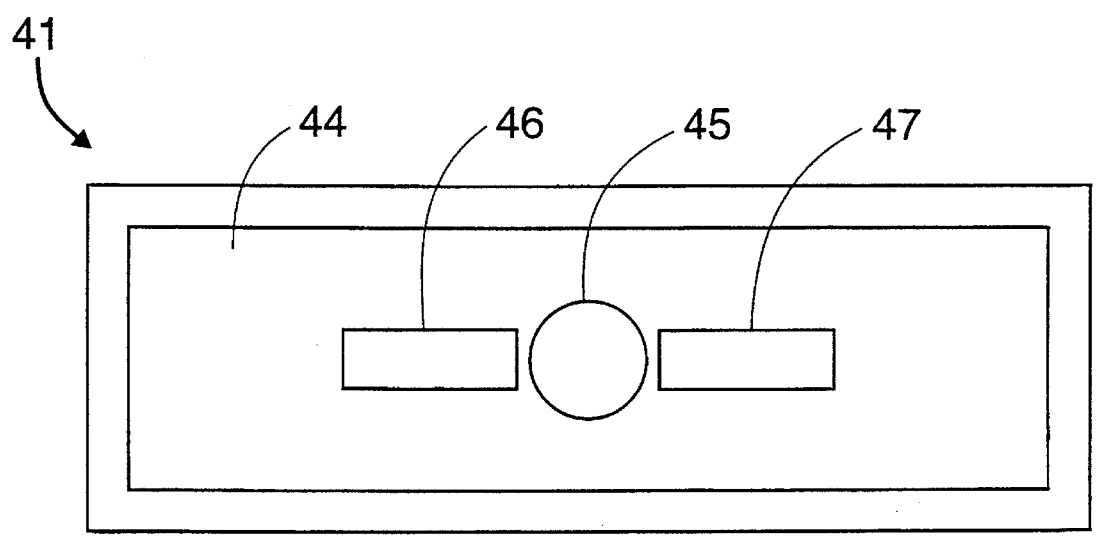
Figure 4:
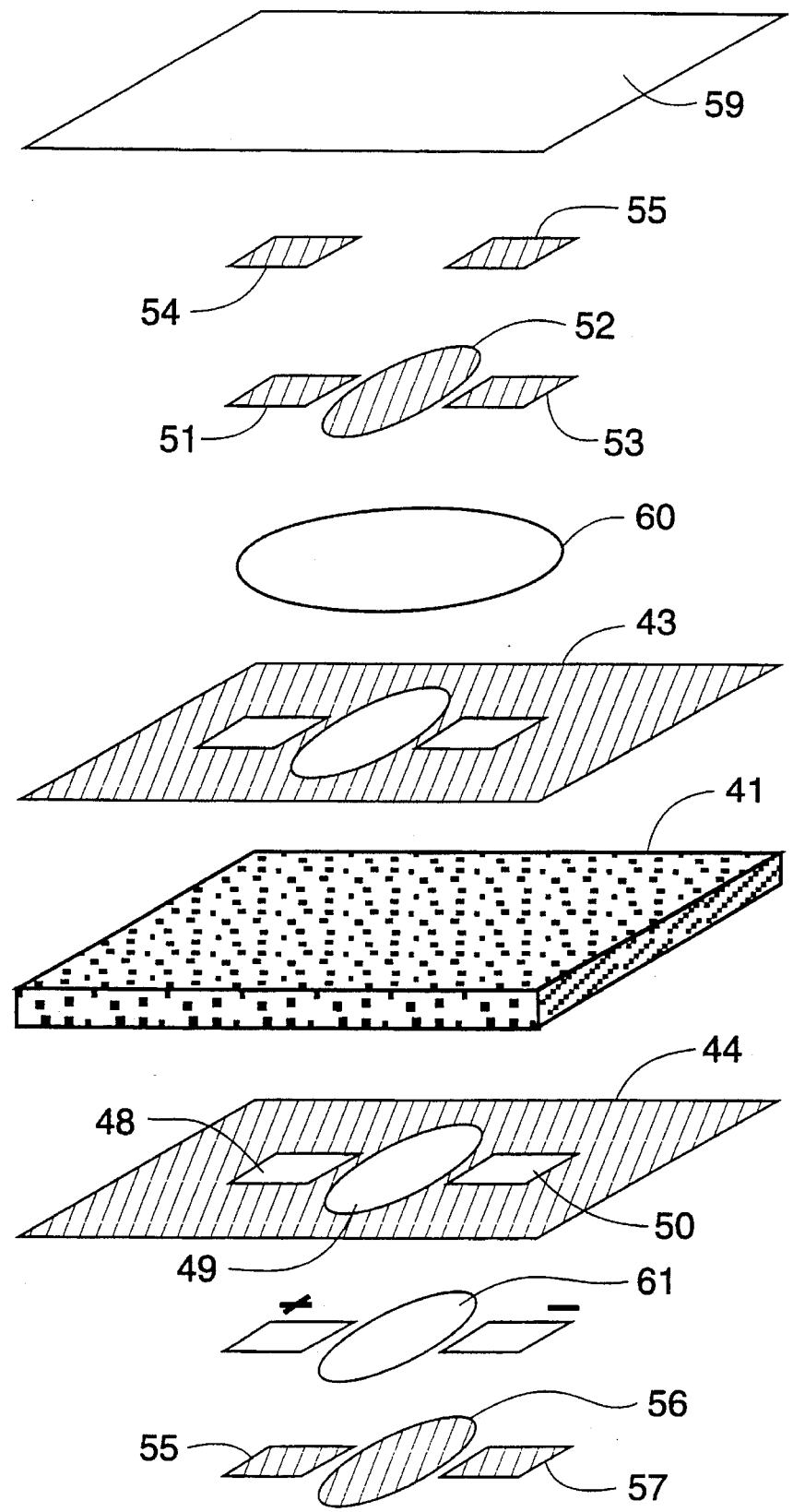
FIG. 4 is an exploded view of the test device of FIGS. 3a and 3b.

FIGS. 3a, 3b and 4 illustrate an example of a panel of the type described in this section. The top or front view as shown in FIG. 3a shows the panel 41 which is a porous sheet, with an oval-shaped sample application area 42 indicated by means of indicia on its upper surface. The bottom or back view of FIG. 3b shows the outline of the lateral sample migration barrier 44 and printed outlines of the test zone 45, the positive control area 46, and the negative control area 47. The sample migration barrier 44 extends to all regions except an outer periphery and the test zone and control areas.

The exploded view of FIG. 4 shows the porous sheet 41 and the shapes of the upper and lower outlines 43, 44 of the lateral sample migration barrier. Although only the outlines are shown, the barrier extends through the full thickness of the porous sheet. The outlines indicate where the barrier material was applied to each surface to penetrate the sheet. Each outline surrounds three untreated zones 48, 49, 50 which form individual channels in top-to-bottom alignment with the test and control areas to permit the sample to diffuse through the sheet only in these areas. On the top or front surface of the panel 41, in alignment with the three diffusion channels, are deposits of a first reagent 51, 52, 53 for the assay. Above the deposit of the first reagent in the positive control area 46 is a deposit of a positive control reagent 54. Likewise, above the deposit of the first reagent in the negative control area 47 is a deposit of a negative control reagent 55. On the bottom or back surface of the panel, in alignment with the three diffusion channels, are deposits of the second reagent 55, 56, 57 for the assay. A protective cover layer 59 protects the upper surface reagent areas. Printed outlines and indicia 60, 61 guide the user in both applying the sample and reading the test results.

For a test for proline iminopeptidase activity, for example, the first reagent in zones 51, 52, 53 may be L-prolyl-beta-naphthylamide, L-prolyl-beta-methoxy-naphthylamide or hydroxy-L-prolyl-beta-naphthylamide, the second reagent in zones 55, 56, 57 may be the visual indicator Fast Garnet, the positive control reagent 54 may be proline iminopeptidase, and the negative control reagent 55 may be a copper salt.

3. Panel Designed for Use With Swab

The third type of test device construction does not rely on forming a liquid migration path for the reagents, either by filling a void space with the liquid sample or diffusing the sample through a penetrable solid material. Instead, a sample applicator which retains a substantial quantity of the sample is used as the transport medium.

The reagents, which in the case of the specific examples discussed above are the conjugate and the indicator, area deposited in separated regions on a common surface so that the swab or other sample-absorptive device, which is wet with the sample, can be drawn across the surface to contact first one and then the other region. Two or more different indicators in discrete regions can be used rather than just one, to permit the simultaneous performance of multiple tests, by drawing the swab across each of the indicator regions subsequent to its contact with the conjugate region.

The reagents may be applied by any of the various different methods discussed above, and may be either immobilized in their respective regions or simply deposited. In the immobilization case, the reagents will remain in their respective regions throughout contact with the sample-laden applicator, except for fragments cleaved from the reagents by one of the assay reactions, such as reporter groups liberated by the action of a hydrolase. In the nonimmobilized case, the first-contacted reagent may be soluble in the sample, and will travel with the sample to the region of the second-contacted reagent, although the presence (or where appropriate, the absence) of the analyte will still be required to achieve a detectable change in the indicator.

The regions can be arranged in geometric patterns for a variety of reasons. The patterns may for example serve as a guide to the user to indicate the direction along which the applicator is to be drawn. Various other effects to be achieved by the geometric pattern will be readily apparent to those skilled in the art.

Figure 5:
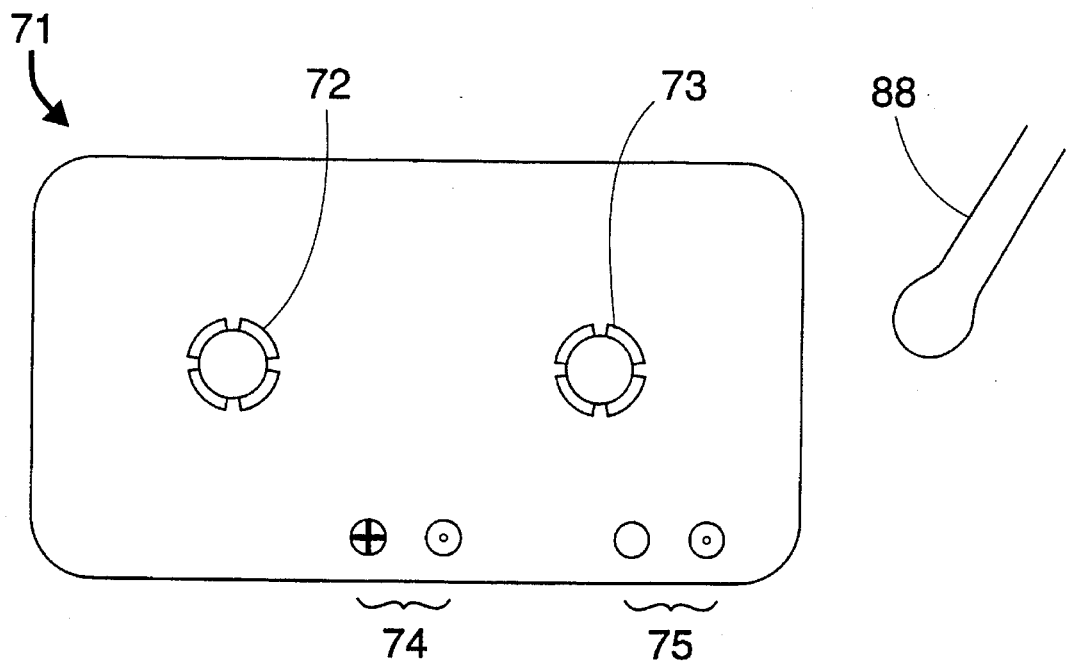
FIG. 5 is a top view of a third type of test device in accordance with the present invention.
Figures 6A, 6B:
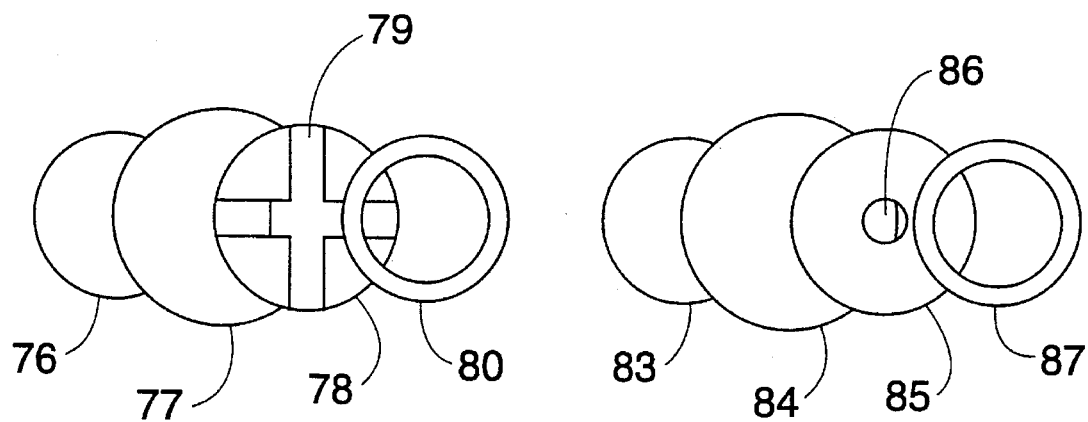
FIG. 6a is a layered view of the components on one of the two sample application zones of the test device of FIG. 5.
FIG. 6b is a layered view of the components of the other sample application zone of the same test device.

An illustration of a panel of the type described in this section appears in FIGS. 5, 6a and 6b. The top view of FIG. 5 shows the panel 71 with two sample application zones—a test zone 72 and a control zone 73, and indicia indicating how the zones will appear for a positive test result 74 and for a negative test result 75. The control zone 73 includes a reagent which will give the same appearance when the sample is applied, regardless of the whether the sample is positive or negative for the analyte, as long as the indicator is functioning. The test zone 72 shows a visible plus sign when the test result is positive and remains blank when the test result is negative.

The components of the test zone 72 are shown as individual layers in FIG. 6a in the order in which they are applied. Using a test for bacterial vaginosis as an example, the bottom layer 76 is the visual indicator Fast Garnet; the layer 77 applied over the indicator is a wetting layer; the layer 78 above the wetting layer is a mask layer which with a hole shaped like a plus-shaped area 79 exposing the underlying indicator for view; and the upper layer 80 is one of the three conjugates.

The components of the control zone 73 as shown in FIG. 6b, again for bacterial vaginosis, are the visual indicator Fast Garnet as the bottom layer 83; the wetting layer 84 applied above the indicator; the mask layer 85 applied above the wetting layer, with a hole 86 in the center; and the control reagent 3-amino naphthoate 87 as the top layer.

To perform the test, a swab 88 (FIG. 5) saturated with sample is applied to each of the two zones. In each zone, the swab is first rubbed over the zone perimeter, preferably by a circular motion, and then rubbed over the central area of the zone. The appearance of the two zones can then be compared to the indicia to determine whether the test result is positive or negative.

4. General Considerations Pertaining to All Test Devices

In each type of test device, the reagents contained in, or deposited on, the device are preferably selected such that all that is needed to complete the test is the addition of the sample plus a minimal number of additional reagents such as, for example, a developer. In particularly preferred embodiments, however, the device will contain all reagents needed other than the sample, so that performance of the test requires nothing more than addition of the sample.

The indicator is preferably a composition which is substantially insoluble in the liquid sample for which the test is designed, so that the indicator remains stationary throughout the test. For test samples in either aqueous or water-soluble media, therefore, the indicator preferably forms a layer (continuous or discontinuous) which is substantially insoluble in water, or the indicator is incorporated in a matrix which is substantially insoluble in water. In the first of the three devices described above, the indicator is retained in a thin concentrated lamina directly underneath a light-transmitting wall, and a change in the indicator is detectable through the light-transmitting wall in a short period of time, thereby providing both high sensitivity and a fast result.

To improve access of the free reporter group to a water-insoluble indicator, the indicator composition can also include penetration enhancers such as, for example, detergents, salts, sugars, sugar alcohols, polyethylene glycols and other polymers or compounds which are soluble in both water and organic solvents. These penetration enhancers can be incorporated into the indicator lamina in a manner which facilitates access of the reporter group to the indicator, while still maintaining the indicator itself insoluble. As mentioned above, alcohol-soluble manganese salts are preferred penetration enhancers in certain embodiments of the invention.

In addition to the components and structural features described above, preferred test devices of this invention include a built-in positive control, a built-in negative control, or both. In certain constructions, these controls can be arranged to be activated at the same time that the assay itself is performed, all by a single application of the specimen. Detectable indications such as, for example, color changes or the lack thereof, which represent both the controls and the test are all detectable. In the chamber construction, for example, the controls and the test indicator can be arranged such that all color-change indications are detectable through a light-transmitting wall.

The controls can occupy positions on the device which are horizontally adjacent to the test area. In the case of the chamber device construction, the controls are preferably horizontally adjacent to the sample application port. Regardless of the construction of the device and the location of the controls, however, the device can contain appropriate indicia to identify the control indicator areas and differentiate them from the test indicator areas. Alternatively, the differentiation can be made obvious by the overall geometric design of the test.

The controls themselves may consist of individual layers or deposits on the solid support, the layers or deposits containing reagents or other appropriate species which will either induce the detectable change in the indicator by themselves or prevent the change from occurring, and will do so only when the test sample is present and yet independently of the presence or absence of the suspect hydrolase or hydrolase inhibitor in the test sample. The optimal choice of reagents to be used as controls and the optimal locations of these controls on or in the device will vary from one test to the next.

Further preferred embodiments of the test devices of the invention contain additional features to enhance the performance of the test. A surface-active agent for example may be applied along the sample contact surface or surfaces of the device. The surface-active agent may be included as a dry solute in a support matrix which forms the lamina immediately underneath the surface, or a coating applied over the surface and beneath any reagents present on the surface. In some cases, the lamina will also contain one or more reagents taking part in the test reactions. In other cases, the surface-active agent will be the sole functional component of the lamina.

Surface-active agents will be useful for specimens which are water-based, as most biological specimens are. Suitable surface-active agents can be solids, semi-solid waxes, or liquids absorbed into solids, and a wide variety of substances which have a surface-active effect may be used. The substances will generally be detergents, wetting agents or emulsifiers, and will vary widely in chemical structure and electronic character, including anionic, cationic, zwitterionic and nonionic substances. Examples are alkyl alkoxy sulfates, alkyl aryl sulfonates, glycerol fatty acid esters, lanolin-based derivatives, polyoxyethylene alkyl phenols, polyoxyethylene amines, polyoxyethylene fatty acids and esters, polyoxyethylene fatty alcohols and ethers, poly(ethylene glycol) fatty acids and esters, polyoxyethylene fatty esters and oils, polyoxypropylene/polyoxyethylene condensates and block polymers, sorbitan fatty acid esters, sulfo derivatives of succinates, alkyl glucosides, and cholic acid derivatives. Trade names of some of the products falling within these classes are Lubrol, Brig®, Tween®, Tergitol®, Igepal®, Triton®, and Teepol.

Test devices may also include additives which enhance stability and shelf-life and which facilitate dissolution of the catalytically active hydrolase or other components which function best when in solution. Examples of such additives are antioxidants (BHT, BHA, ascorbate, dithiothreitol), metal binding components and chelators (EDTA, EGTA), other components which facilitate the dissolution of the various components (mannitol, sorbitol, polyethylene glycol, lactose), and buffers.

In test devices where the solid-phase reagents are applied as laminae, these laminae may be formed by applying the lamina material in liquid form followed by drying or other solidification. The liquid form of the reagent may be, for example, a solution or suspension of the reagent, or an uncured liquid form of the lamina matrix precursor, and the solidification step may thus be an evaporation of the solvent or suspending liquid or a curing of the matrix precursor. Additional materials may be included in the lamina for a variety of purposes, such as for example:

(1) to facilitate the application of the liquid to the surface by modifying the viscosity of the liquid, (2) to help form a continuous smooth solid layer which remains uniform and does not disintegrate or granulate over time or upon the application of additional layers over it, (3) to modify the solubility of the layer with solvents used in layers to be applied over it or to make the layer soluble in solvents which do not dissolve layers applied underneath.

or all of these. Polymeric materials are preferred additives to serve one or all of these purposes. Examples are celluloses or polyacrylates and various derivatives thereof, with the substitutions appropriately selected to achieve the desired solubility characteristics. For those test devices designed for aqueous or other water-based samples, the indicator lamina preferably contains the indicator retained in a matrix of solid material which is largely insoluble in water. This prevents the indicator from migrating out of the lamina and thereby dropping in concentration. Alternatively, an indicator which is insoluble in water and which will form a coherent lamina which will remain intact by itself can be used.

For those embodiments of the invention in which a positive control indicator, a negative control indicator or both are included in the device, one or more additional reagents will be included for each control. These additional reagents will either be incorporated within one of the existing laminae in a horizontally defined portion of that lamina or applied as a separate, vertically adjacent lamina over a horizontally defined portion of the existing lamina. By virtue of their position on or in the device, these additional reagents define control areas which are horizontally separated from each other and from the test area.

The selection of an appropriate reagent for a positive or negative control will depend on a variety of factors, including the analyte which the test is designed to detect, the availability of control materials, the type of indicator used to detect the presence of the analyte, and whether the reagent is intended to serve as a positive control or a negative control. By utilizing known chemistries, the selection of an appropriate reagent will in most cases be apparent to those skilled in the art.

A positive control for a hydrolase test, for example, may be a sample of the hydrolase itself, a hydrolase with similar hydrolytic action, the reporter group or one of its analogues, or any other species with a parallel mode of action which initiates or induces the reaction or reaction sequence which culminates in a detectable change in the indicator. While the preferred positive control for hydrolase tests on human specimens is a hydrolase isolated from human sources, human hydrolase is often not available. A similar hydrolase isolated from animal, plant or microbial sources can then be employed. When the positive control is a sample of the reporter group or an analog or derivative of the reporter group, the control reacts with the indicator to generate a signal. This type of positive control can be used to assure the performance of the indicator, which is often the most critical or the least stable test component of the system.

The negative control for a hydrolase test may be a denaturing, inhibiting or otherwise hydrolase-inactivating agent which prevents or blocks the reaction or reaction sequence, and thereby prevents the detectable change from occurring regardless of whether or not the catalytically active hydrolase is present in the sample or specimen. Alternatively, the negative control reagent may preferentially react with the free reporter group or the indicator, thereby preventing any interaction between them which would generate a detectable signal. In test devices designed for hydrolases, the preferred negative control is a highly specific inhibitor of the hydrolase whose presence is being detected. If such an inhibitor is not available, a less specific hydrolase inhibitor can be used, one which inhibits a number of hydrolases, including the hydrolase whose presence is being sought. Inhibitors of this type include class-specific protease inhibitors such as for example thiol, serine, metallo- and aspartic protease inhibitors, denaturants such as, for example, detergents, inactivating metallo-compounds, and acids and bases. Alternatively, the negative control can incorporate a component which preferentially reacts with the reporter group or with the indicator, thereby preventing their interaction to generate a signal. The choice of appropriate positive and negative control elements for use in the test devices of the present invention are based on factors known to those of skill in the art.

Positive and negative controls serve at least three important functions:

(a) First, a properly functioning positive control provides assurance that all test elements (the conjugate, the indicator and the reaction conditions) are performing correctly, and can be relied upon to detect a hydrolase in a specimen, if the hydrolase is indeed present. Similarly, a properly functioning negative control provides assurance that the test reagents can be relied upon not to generate a positive result in the absence of the hydrolase. As such, the positive and negative controls serve as reagent controls.

(b) Second, a properly functioning positive control provides assurance that the specimen being tested does not contain interferents which can inhibit the hydrolase or, by other means, prevent it from generating a positive test result. Similarly, a properly functioning negative control provides assurance that the specimen being tested does not contain interferents which can generate a positive signal in the absence of the hydrolase. As such, the positive and negative controls serve as specimen controls.

(c) Third, if a test device and its controls are designed and constructed such that the control elements of the device are geometrically and temporally the last portions of the test device to be contacted by the specimen, a properly functioning positive control provides an indication that the test device has been filled, or properly wetted, with the specimen. Thus, in this case, the positive control serves as a procedural control. This consideration is particularly important with clear or colorless specimens (such as, for example, vaginal fluid or saliva), in devices designed to contain small volumes and in devices in which specimen flow paths are partially obstructed from view.

Analogous functions for analytes other than hydrolases are similarly served by the inclusion of positive and negative controls.

Preferably, the test device is designed such that both controls are activated when the specimen is applied to the test device for the test itself. In some cases, this is achieved most effectively by placing the control reagents and the test reagents on the same surface of the device. In devices which have a chamber construction, described above as the first of the three types of device, the control areas may for example be arranged as extensions of the test area or sample application port, all contained in the same chamber with unobstructed fluid communication between the various areas. When both positive and negative control areas are included, the control areas can be separated from each other by the test area or by the sample application port which is positioned in between the two. All areas are then filled with sample by a single sample application. When the upper wall of the chamber is of a light-transmitting material, the detectable changes, or absence thereof, are readily detectable, and the identification of areas as positive and negative controls is conveniently achieved by placing appropriate indicia on the outer surface of the device. In some cases, effective results can also be achieved when the control reagents are placed in laminae on the chamber surface opposite that which bears the other reagent(s), such that the control reagent and the remaining reagent(s) are separated by the air gap.

In devices of the invention in general, the control areas of the device will contain all components and reagents used in the test area with the addition of the control reagents, either incorporated in horizontally delineated sections of one or more of the same laminae used in the test area or applied as separate laminae over such horizontally delineated sections. To achieve sharp boundaries for the control areas and to prevent the control reagents from activating or deactivating the test area, it is often beneficial to place discontinuities in the laminae at the boundaries separating the control areas from the test area to minimize or eliminate the possibility of lateral diffusion of the control reagents out of their respective control areas.

Test devices of the present invention are preferably flat and thin and of a size which are easily held by hand. For those test devices which include a chamber, the chamber depth is not critical to the invention any may vary. In most cases, however, a chamber ranging from about 3 mil to about 50 mil (0.003–0.050 inch: 0.0076–0.127 cm) in depth, preferably from about 5 mil to about 15 mil (0.005–0.0.015 inch; 0.0127–0.0381 cm), will give the best results. For any given depth, the lateral dimensions of the chamber (i.e., the spacing between its side walls) will define the size of the sample which the device will accommodate, and are otherwise unimportant except to define the size and shape of the visible test area on the outer surface of the device. The lateral dimensiosn should thus provide a test area which is large enough to be seen, and yet small enough that the chamber which will be completely filled by a specimen of reasonable size. The specimen size will vary with the type of specimen and its source and method of sampling. In typical structures, it is contemplated that the lateral area of the chamber will range from about 0.1 cm$^2$ to about 10 cm$^2$, or preferably from about 0.3 cm$^2$ to about 3 cm$^2$. The internal volume of the chamber in typical structures will likewise vary, and for most types of samples, volumes ranging from about 3 μL to about 300 μL will be the most appropriate and convenient.

In all types of test devices disclosed herein, cover sheets serving as barriers to air, moisture, light or all three may be included to provide the device with desired rigidity and to enhance long-term storage properties. In devices in which the support panel itself is porous, for example, the panel containing the reagent laminae and indicator laminae can be laminated or otherwise sealed between two non-porous cover sheets of plastic, aluminum foil, waterproofed cardboard or other comparatively rigid materials to provide structural strength as needed. These rigid cover sheets can be light-transmitting or opaque, as desired. If the sheet is opaque, holes can be cut in the material to permit either sample addition, test evaluation, or both. For light-transmitting cover sheets, a sampel entry hole can be made in the sheet for sample application, and test interpretation can be made directly through the same sheet, preferably through a clear, transparent zone on the sheet. Indicia can be printed or labeled onto cover sheets in a manner which provides the user with instructions for using the device. Cover sheets can also be peel-off laminae of aluminum foil, metallized Mylar® or other material to prevent or minimize exposure of reactive components in the device to light, air, and moisture.

The test device of the present invention is highly versatile and can be used for a wide range of assays and chemical reactions, depending on the particular analyte whose presence or absence is sought to be determined. The reagents occupying the laminae in the test device may thus be enzymes, co-factors, enzyme substrates such as cleavable conjugates, proteins and smaller organic molecules, and organic reagents in general. Likewise, the reaction which the analyte initiates in, or undergoes with, the reagent may be an enzymatic or non-enzymatic reaction such as a hydrolysis or other type of cleavage, an oxidation reaction, a reduction reaction, or any of a wide array of other types of reactions. The analyte may be any species whose presence, absence or level is indicative of a condition. Analytes may thus be organic compounds, inorganic compounds, enzymes, cofactors, proteins or various kinds, viruses, microorganisms, and any other species which might be present in a sample.

The following examples are offered by way of illustration only.

EXAMPLES

Materials used in the experiments were prepared as follows:

A. PREPARATION OF DIAZONIUM DYE INDICATOR LAMINAE

1. MATERIALS
   a. Fast Garnet GBC, Fast Red B, Fast Black K, Fast Dark Blue, Fast Bordeaux, Fast Violet or other diazonium dye.
   b. 1.7M $MnCl_2$ in ethanol.
   c. 10% (wt/wt ethylcellulose in ethanol).
   d. 10% (wt/vol) Lubrol in water.
   e. #5, #10, #20 or #30 Meyer Rods.
   f. Mylar® sheets either 5 mil, 10 mil, or 14 mil thick.
   g. Mylar® (5 or 7 mil):polyethylene (2 or 3 mil) laminated sheets.

2. PROCEDURES

The solid dyes were weighed into test tubes (10–100 mg) and 100 µL $MnCl_2$ solution and 900 µL ethylcellulose solution were added to each tube. The suspensions were heated to dissolve the dyes, cooled, and centrifuged to remove insoluble debris. Supernatant dye solutions were formed into thin coatings on Mylar® sheets or on Mylar®:polyethylene laminates with Meyer Rods. The coatings were air dried and stored at room temperature until used. Coating thickness was controlled by the Meyer Rod used (coating thickness increasing with Meyer Rod number).

B. PREPARATION OF CONJUGATE LAMINAE

1. MATERIALS
   a. Conjugates:
      (1) L-prolyl-beta-naphthylamide (PRO.NAM).
      (2) L-glycyl-L-prolyl-4-methoxynaphthylamide (GLY-PRO.MNA).
      (3) N-benzyloxycarbonyl-L-prolyl-beta-naphthylamide (Z-PRO.NAM).
      (4) hydroxy-L-prolyl-beta-naphthylamide (HYDROXYPRO.NAM).
      (5) L-arginyl-beta-naphthylamide (ARG.NAM).
      (6) N-benzyloxycarbonyl-L-arginyl-L-prolyl-beta-naphthylamide (Z-ARG.PRO.NAM).
      (7) Tert-butyloxycarbonyl-L-valyl-L-leucyl.L-lysyl-7-amino-4-methyl coumarin (T-boc.VAL.LEU.LYS.AMC).
   b. Other materials:
      (1) 0.8M NaOH.
      (2) 10% (wt/vol) Lubrol in water.
      (3) 7% (wt/wt) hydroxypropylcellulose in ethanol.
      (4) Mylar® sheets either 5 mil, 10 mil, or 14 mil thick.
      (5) Mylar® (5 or 7 mil):polyethylene (2 or 3 mil) laminated sheets.

2. PROCEDURES

Solid conjugate was suspended in a mixture of 100 microliters of solvent (water, ethanol, or dimethyl formamide), 800 microliters hydroxypropylcellulose solution, and 50 microliters of sodium hydroxide solution. The suspension was heated to completely dissolve the conjugate, and the cooled solution was coated onto the solid sheet as described in PREPARATION A.

C. PREPARATION OF MANUALLY ASSEMBLED HYDROLASE TEST DEVICES

1. MATERIALS
   a. diazonium dye indicator laminae on 5 mil Mylar® sheets (PREPARATION A).
   b. conjugate laminae on 5 mil Mylar® sheets (PREPARATION B).
   c. untreated 14 mil Mylar® sheets.
   d. double sided adhesive tape.

2. PROCEDURES

Double sided tape was affixed over the entire top and bottom surfaces of a 14 mil thick solid Mylar® sheet, and a 0.3125 inch in diameter hole was punched through the entire triple laminate (adhesive tape-Mylar®-adhesive tape). The 14 mil Mylar® sheet served as a spacer between a top sheet of 5 mil Mylar® containing a diazonium dye indicator lamina, and a bottom 5 mil Mylar® sheet containing a conjugate lamina. After being adhered to the 14 mil Mylar® spacer sheet by means of the double sided adhesive, the top and bottom sheets served as top and bottom of a chamber. The conjugate lamina on Mylar® was adhered to the bottom surface of the double sided, adhesive-covered 14 mil Mylar® sheet with the conjugate lamina facing upward. The walls of the hole punched in the 14 mil Mylar® sheet and the bottom mylar sheet formed a small receptacle, 14 mil deep and 0.3125 inches in diameter. The bottom surface of the receptacle was covered with a lamina containing a conjugate. A smaller circular hole (0.125 inches in diameter) was punched in the third Mylar® sheet containing the diazonium dye indicator lamina, and this third Mylar® sheet was adhered to the top surface of the 14 mil Mylar® sheet covered with double sided tape in such a fashion that the diazonium dye indicator lamina formed the inner surface of a top of the receptacle described above, and also such that the small hole in the third sheet was centered over the receptacle described above. The resulting laminated panel functioned as a test device, containing a receptacle with a top and bottom. The inner surface of the receptacle top included a thin, largely insoluble indicator dye lamina containing a visual indicator in a water insoluble matrix, and the inner surface of the receptacle bottom included a thin lamina of water soluble conjugate. The receptacle was a void space until a liquid sample was added. When an aqueous sample was added to the device, the water soluble conjugate was solubilized, but the diazonium dye indicator lamina remained intact as a thin film. If a hydrolase capable of hydrolyzing the conjugate was present in the sample, the conjugate was hydrolyzed to release free reporter group (4-methoxy naphthylamine, beta-naphthylamine, or 7-amino-4-methyl coumarin), which reacted with the insolubilized diazonium dye indicator lamina to form a color in a lamina on the inner top surface of the device.

D. PREPARATION OF PARADIMETHYLAMINOCINNAMALDEHYDE (PDMAC) HIGH BUFFER CAPACITY CHROMOGEN SOLUTION MATERIALS AND PROCEDURES

The following solutions were mixed sequentially as indicated and the resulting solution stored at 4 degrees C. until needed.
   a. 100 µL 25 mM para-dimethylaminocinnamaldehyde in ethanol.
   b. 6.75 mL 1M citric acid solution in water.
   c. 2.25 mL 2M disodium phosphate in water.
   d. 900 µL 10% (wt/wt) sodium dodecyl sulfate in water.

E. PREPARATION OF PARADIMETHYLAMINOCINNAMALDEHYDE (PDMAC) CONCENTRATED ACID

CHROMOGEN SOLUTION MATERIALS AND PROCEDURES

The following materials were mixed sequentially as indicated and the resulting solution stored at 4 degrees C. until needed.
  a. 80 mL distilled water.
  b. 5.6 mL glacial acetic acid.
  c. 435 µL 5M NaOH (to adjust pH to 4.5).
  d. 13 mL distilled water.
  e. dry sodium dodecyl sulfate to make a final concentration of 1.0% (wt/wt).
  f. 1 mL 50 mM para-dimethylaminocinnamaldehyde.

F. PREPARATION OF PARADIMETHYLAMINOCINNAMALDEHYDE (PDMAC) DILUTE ACID CHROMOGEN SOLUTION MATERIALS AND PROCEDURES

The following materials were mixed sequentially as indicated and the resulting solution stored at 4 degrees C. until needed.
  a. 30 mL distilled water.
  b. 2.8 mL glacial acetic acid.
  c. approximately 435 µL 5M NaOH (to adjust pH to 3.0).
  d. 10 mL (10% wt/wt) sodium dodecyl sulfate solution in water.
  e. 1 mL 25 mM para-dimethylaminocinnamaldehyde in ethanol.
  f. distilled water to make a total volume of 50 ml.

G. PREPARATION OF BACTERIAL CELL SUSPENSIONS

Pure cultures of *Mobiluncus curtisii*, ATCC strain 35241 and *Mobiluncus mullieris* ATCC strain 35239 were grown anaerobically on sterile Brucella Blood Agar in petri dishes at 37° C. for 4–8 days. The cells scraped from the surface of 10 petri dishes were suspended in 2.5 mLs 150 mM saline and frozen until used.

Pure cultures of *Candida albicans*, ATCC strain 28366 were grown in liquid culture medium as indicated by Odds, F. C., *J. Gen. Microbiol.*, 129:431–438 (1983). The cells were suspended in 2.5 mL 150 mM saline and frozen until used.

EXPERIMENT I

This experiment tests the comparative ability of Fast Garnet GBC solutions and Fast Garnet GBC chromogenic indicator laminae to detect the reporter group, 2-naphthylamine.

A. MATERIALS
  1. 100 mM Tris buffer, pH 7.0.
  2. 0.15% (wt/vol) Fast Garnet GBC solution in water.
  3. The reporter group 2-naphthylamine dissolved in water at the concentrations shown.
  4. Fast Garnet GBC indicator laminae (#20 Meyer Rod, PREPARATION A).

B. PROCEDURES
  1. Testing of Fast Garnet GBC indicator solutions
  Twenty five µL Tris buffer and 25 µL water were added to duplicate wells of microtiter plates, followed by 50 µL of the reporter group, 2-naphthylamine, solutions at the concentrations shown. Finally, 50 µL Fast Garnet GBC solution was added to each well, and the color formation noted after 5 minutes.
  2. Testing of Fast Garnet GBC indicator laminae
  Twenty five µL Tris buffer and 25 µL water were added to duplicate wells of microtiter plates, followed by 50 µL of the reporter group, 2-naphthylamine, solutions at the concentrations shown. After mixing, 20 µL of the mixture was transferred to a Fast Garnet GBC indicator lamina, and the color formation noted after 5 minutes.

TABLE I

| COLOR SCORE | INTERPRETATION |
| --- | --- |
| − | no red color formation |
| +/− | possible red color formation |
| + | clearly visible red color formation |
| ++ | extremely intense red color formation |

C. RESULTS
  1. Fast Garnet GBC Chromogenic Liquid Reagent
  A 2-naphthylamine solution at 1.25 micrograms/100 microliters produced a clearly detectable red color in the solution, but no color formed at lower concentrations of 2-naphthylamine.
  2. Fast Garnet GBC cromogenic indicator laminae
  A 2-naphthylamine solution at 0.3 micrograms/100 microliters produced a clearly detectable red color in the Fast Garnet GBC indicator laminae, but no color formed at lower concentrations of 2-naphthylamine.

TABLE 2

| ADDITIONS | MICROLITER WELLS | | | | |
| --- | --- | --- | --- | --- | --- |
| VOLUME (µL) | 1 | 2 | 3 | 4 | 5 |
| Tris Buffer | 25 | 25 | 25 | 25 | 25 |
| Water | 25 | 25 | 25 | 25 | 25 |
| Naphthylamine | 50 | 50 | 50 | 50 | 50 |
| (µg Naphthylamine) | 2.5 | 1.25 | 0.6 | 0.3 | 0.15 |
| Fast Garnet | 50 | 50 | 50 | 50 | 50 |
| Fast Garnet Color | + | + | − | − | − |
| Liquid Reagent | + | + | − | − | − |
| Fast Garnet Color | + | + | + | + | − |
| Solid Reagent | + | + | + | + | − |

D. INTERPRETATION

The Fast Garnet GBC chromogenic indicator laminae were at least four times as sensitive to the reporter group, 2-naphthylamine, as the Fast Garnet GBC liquid chromogenic reagent used in published clinical studies. This increased sensitivity can be utilized in either of two ways: (1) it can be utilized to detect lower concentrations of the reporter group, 2-naphthylamine, hydrolytically released from a conjugate; or, (2) it can be used to decrease the incubation time required to detect hydrolase-catalyzed release of the reporter group, 2-naphthylamine, from a conjugate.

EXPERIMENT II

This experiment tests the comparative ability of a liquid Fast Garnet GBC chromogenic indicator and a Fast Garnet GBC laminae-based chromogenic indicator to detect proline iminopeptidase activity in *Mobiluncus curtisii* ATCC strain 35241 cells.

A. MATERIALS
  1. Buffers:
    a. 100 mM Tris buffer, pH 7.0.
    b. 100 mM sodium phosphate buffer, pH 7.0
  2. 0.2% (wt/vol) conjugate, e.g., L-prolyl-beta-naphthylamide (PRO.NAM) dissolved in water.
  3. 0.15% (wt/vol) Fast Garnet GBC solution in water.
  4. Fast Garnet GBC chromogenic indicator laminae (#20 Meyer Rod, PREPARATION A).
  5. *Mobiluncus curtisii* ATCC strain 35241 suspension (PREPARATION G).

B. PROCEDURES

1. Testing of solution-based systems

Twenty five microliters of Tris buffer and twenty five μL conjugate solution (i.e., PRO.NAM) in water were added to duplicate wells of a microtiter plate, followed by 50 μL *Mobiluncus curtisii* ATCC strain 35241 cell suspension diluted as shown. The suspension was incubated at 25° C. for four hours, and 50 μL Fast Garnet GBC solution was added to each well. Color formation was noted after 5 minutes.

2. Testing of Fast Garnet GBC chromogenic indicator laminae

Twenty five microliters of phosphate buffer and twenty five μL conjugate solution (e.g., PRO.NAM) in water were added to duplicate wells of a microtiter plate, followed by 50 μL *Mobiluncus curtisii* ATCC strain 35241 cell suspension diluted as shown. The suspension was incubated at 25° C. for four hours, and a 20 μL aliquot was removed and added to Fast Garnet GBC chromogenic indicator laminae. Color formation was noted after 5 minutes.

TABLE 3

| COLOR SCORE: | INTERPRETATION |
|---|---|
| − | no red color formation |
| +/− | possible red color formation |
| + | clearly visible red color formation |
| ++ | extremely intense red color formation |
| ND | not done |

C. RESULTS

1. Fast Garnet GBC Liquid Reagent

The liquid Fast Garnet GBC chromogenic indicator produced a barely detectable red color with the undiluted *Mobiluncus curtisii* ATCC strain 35241 cell suspension. No red color was seen when the cell suspension was diluted 1:2 with saline.

2. Fast Garnet GBC chromogenic indicator laminae

The Fast Garnet GBC chromogenic indicator laminae produced a clearly detectable red color even when the *Mobiluncus curtisii* ATCC strain 35241 suspension was diluted 1:4 with saline prior to incubation with the proline iminopeptidase-hydrolyzable conjugate, PRO.NAM. No red color was seen when the cell suspension was diluted 1:8 with saline.

D. INTERPRETATION

*Mobiluncus curtisii* ATCC strain 35239 cells exhibit the ability to hydrolyze the proline iminopeptidase-hydrolyzable conjugate, PRO.NAM, releasing the reporter group, 2-naphthylamine. The reporter group is able to produce a red color upon interaction with Fast Garnet GBC, either in solution, or as a dry lamina. The Fast Garnet GBC chromogenic indicator laminae are at least four times as sensitive to *Mobiluncus curtisii* ATCC strain 35241 proline iminopeptidase activity as the Fast Garnet GBC liquid chromogenic reagent utilized in published clinical studies. This increased sensitivity can be utilized in either of two ways: (1) it can be utilized to detect lower concentrations of proline iminopeptidase activity; or, (2) it can be used to decrease the incubation time required to detect proline iminopeptidase activity.

EXPERIMENT III

This experiment tests the capacity of alternative dried diazonium dye laminae to detect the reporter group, beta-naphthylamine and to detect *Mobiluncus curtisii* ATCC strain 35241 cell-catalyzed hydrolysis of the proline iminopeptidase-hydrolyzable conjugate, L-prolyl-beta-naphthylamide, the conjugate also present as a dried lamina.

A. MATERIALS

1. Fast Garnet GBC, Fast Red B, Fast Black K, Fast Dark Blue, Fast Violet, and Fast Bordeaux indicator laminae prepared as described in PREPARATION A (#20 Meyer rod).

2. pure *Mobiluncus curtisii* ATCC Strain 35241 culture grown as described in PREPARATION G and suspended in 100 mM NaCl solution.

3. proline iminopeptidase-hydrolyzable conjugate, i.e., the L-prolyl-beta-naphthylamide, laminae prepared as described in PREPARATION B (Number 20 Meyer Rod).

4. manually assembled prototypes using each of the diazonium dye indicator laminae (item 1 above) and L-prolyl-beta-naphthylamide laminae (item 3) as described in PREPARATION C.

5. 50 mM reporter group, beta-naphthylamine, in water

B. PROCEDURES

Chromogenic indicator laminae of Fast Garnet GBC, 15 mg; Fast Black K, 57 mg; Fast Dark Blue, Fast Bordeaux, Fast Violet, and Fast Red B, 21 mg prepared as described in PREPARATION A and proline iminopeptidase-hydrolyzable conjugate, L-prolyl-beta-naphthylamide, (13 mg/ml)

TABLE 4

| COMPONENTS | AMOUNT PER WELL | | | | | | | | | |
|---|---|---|---|---|---|---|---|---|---|---|
| WELL NO.: | 1 | 2 | 3 | 4 | 5 | 6 | 7 | 8 | 9 | 10 |
| Tris Buffer (μL) | 25 | 25 | 25 | 25 | 25 | ND | ND | ND | ND | ND |
| Phosphate Buffer (μL) | ND | ND | ND | ND | ND | 25 | 25 | 25 | 25 | 25 |
| Cells (μL) | 50 | 50 | 50 | 50 | 50 | 50 | 50 | 50 | 50 | 50 |
| Cell Dilution (μL) | 0 | 2 | 4 | 8 | 16 | 0 | 2 | 4 | 8 | 16 |
| Conjugate (μL) | 25 | 25 | 25 | 25 | 25 | 25 | 25 | 25 | 25 | 25 |
| Fast Garnet GBC (μL) | 50 | 50 | 50 | 50 | 50 | ND | ND | ND | ND | ND |
| Incubation (hours) | 4 | 4 | 4 | 4 | 4 | 4 | 4 | 4 | 4 | 4 |
| INDICATOR | TEST RESULTS (DUPLICATES) | | | | | | | | | |
| Fast Garnet GBC Color | +/− | − | − | − | − | ND | ND | ND | ND | ND |
| Liquid Reagent | +/− | − | − | − | − | ND | ND | ND | ND | ND |
| Fast Garnet Color | ND | ND | ND | ND | ND | + | + | + | − | − |
| Solid Reagent | ND | ND | ND | ND | ND | + | + | + | − | − | prepared as described in PREPARATION B were manually assembled into test devices (PREPARATION C).

1. Tests of device performance with the reporter group, beta-naphthylamine.

Approximately 40 microliters of 500 micromolar beta-naphthylamine solution was added to the manually assembled kits. After 10 minutes, color formation was noted.

2. Test kit performance with proline iminopeptidase activity in *Mobiluncus curtsii* ATCC strain 35241 cells.

Approximately 40 microliters of the *Mobiluncus curtisii* ATCC strain 35241 suspension were added to each test kit. After 10 minutes at room temperature, the appearance of color was determined.

C. RESULTS

Strong color formation occurred when either a solution of the reporter group, beta-naphthylamine, or a *Mobiluncus curtisii* ATCC strain 35241 suspension was added to the test devices employing dried lamina containing the proline iminopeptidase-hydrolyzable conjugate (PRO.NAM) and chromogenic indicator laminae of Fast Garnet GBC, Fast red B, Fast Black K, Fast Dark Blue and Fast Bordeaux. No color formed when a solution of the reporter group, beta-naphthylamine, or a suspension of *Mobiluncus curtisii* ATCC strain 35241 cells were added to test devices containing Fast Violet indicator laminae. Water did not produce a color with any of the devices tested.

TABLE 5

| Dyes | Water | beta-Naphthylamine | Mobiluncus Curtisii |
| --- | --- | --- | --- |
| Fast Garnet GBC | no color | red | red |
| Fast Black K | no color | black | black |
| Fast Red B | no color | purple | purple |
| Fast Dark Blue | no color | blue | blue |
| Fast Violet | no color | no color | no color |
| Fast Bordeaux | no color | red | red |

D. INTERPRETATION

1. Chromogenic indicator laminae containing Fast Garnet GBC, Fast Black K, Fast Red B, Fast Dark Blue, and Fast Bordeaux can detect beta-naphthylamine colorimetrically.

2. *Mobiluncus curtisii* ATCC strain 35241 cells contain proline iminopeptidase activity which hydrolyzes the conjugate, L-prolyl-beta-naphthylamide, present in a dried lamina to release the reporter group, beta-naphthylamine.

3. Dry chromogenic indicator laminae containing appropriate diazonium dyes detect the released reporter group, 2-naphthylamine, thereby detecting proline iminopeptidase activity.

4. Test devices can be constructed using a dried diazonium dye chromogenic indicator lamina and a dried L-prolyl-beta-naphthylamide conjugate lamina to permit detection of proline iminopeptidase activity upon addition of a liquid specimen.

5. Not all diazonium indicators can be used as chromogenic indicators for the reporter group, 2-naphthylamine (e.g., Fast violet). The selection of a specific chromogen will depend on many factors known to those skilled in the art, including stability, test color intensity with a reporter group, color of specimen, and cost.

EXPERIMENT IV

This experiment tests alternative conjugates for hydrolysis by microbial cells (*Mobiluncus curtisii* ATCC strain 35241, *Mobiluncus mulieris* ATCC strain 35239, *Candida albicans* ATCC strain 28366) and enzymes.

A. MATERIALS

1. Fast Garnet GBC chromogenic indicator laminae prepared as described in PREPARATION A (#20 Meyer rod).

2. organisms:
   a. pure *Mobiluncus curtisii* ATCC Strain 35241 culture grown as described in PREPARATION G and suspended in 100 mM NaCl solution.
   b. pure *Mobiluncus mullieris* ATCC Strain 35239 culture grown as described in PREPARATION G and suspended in 100 mM NaCl solution.
   c. pure *Candida albicans* ATCC Strain 28366 culture grown as described in PREPARATION G and suspended in 100 mM NaCl solution.

3. enzymes:
   a. proline iminopeptidase from *Bacillus coagulans* (Sigma).
   b. Pronase (2 commercial sources)

4. conjugates:
   a. 10 mM L-prolyl-beta-naphthylamide (PRO.NAM).
   b. 10 mM L-glycyl.L-prolyl-4-methoxynaphthylamide (GLY.PRO-MNA).
   c. 10 mM N-benzyloxycarbonyl-L-prolyl-beta-naphthylamide (Z-PRO.NAM).
   d. 10 mM hydroxy-L-prolyl-beta-naphthylamide (HYDROXYPRO.NAM).
   e. 10 mM L-arginyl-beta-naphthylamide (ARG.NAM).
   f. 10 mM N-benzyloxycarbonyl-L-arginyl.L-prolyl-beta-naphthylamide (Z-ARG.PRO.NAM).
   g. T-butyloxycarbonyl-L-valyl.L-leucyl.L-lysyl-7-amino-4-methyl coumarin (T-boc.VAL.LEU.LYS.AMC).

5. buffers:
   a. 100 mM tris buffer, pH 8.0.
   b. 500 mM 2-(N-morpholino) ethanesulfonic acid (MES) buffer, pH 5.0
   c. 200 mM acetate buffers, pH 3.0, 3.5, 4.0, 5.0, and 5.5.

6. para-dimethylaminocinnamaldehyde indicators (PREPARATIONS D, E, and F).

B. PROCEDURES

1. Devices containing Fast Garnet GBC chromogenic indicator laminae

10 μL aliquots of the indicated conjugate solution (10 mM) was added to 10 μL buffer at the pH shown. 20 μL of the indicated cell suspension or enzyme solution (proline iminopeptidase from *B. coagulans* or pronase from two separate vendors) was added, and the suspension agitated to mix the contents. After a 10 minute incubation at room temperature, a 10 μL aliquot was added to a Fast Garnet GBC chromogenic indicator lamina. Red color formation was observed at 5 minutes.

2. Tests with PDMAC chromogen in solution

50 μL distilled water, 25 μL buffer, and 25 μL microbial suspension were mixed. 5 μL conjugate was added, and the mixture allowed to incubate for 10 minutes at room temperature. 100 μL PDMAC was added to each incubation, and the color score noted.

TABLE 6

| COLOR SCORE: | INTERPRETATION |
| --- | --- |
| 0 | no red color formation |
| 0.25 | Faintest red color detectable visually |
| 0.5 | Distinct red color |

TABLE 6-continued

| COLOR SCORE: | INTERPRETATION |
|---|---|
| 1.0 | Red color between 1.0 and 2.0 in intensity |
| 2.0 | Darkest red color possible in test system |
| nd | not done |

C. RESULTS

TABLE 7

| CONJUGATES | M. MULLIERIS FAST GARNET COLOR SCORE (pH) | M. CURTISII FAST GARNET COLOR SCORE (pH) | M. CURTISII PDMAC COLOR (PREP. pH) | C. ALBICANS FAST GARNET COLOR SCORE (pH) |
|---|---|---|---|---|
| PRO.NAM | 1 (pH 8.0) | 2 (pH 5.0); 1 (pH 8.0) | 2 (D,E, pH 4.5–8.0) | 0.50 (pH 5.0, 8.0) |
| PRO.METHOXY. NAM | ND | 0 (pH 3.0–4.5) | 0 (E, pH 3.0–7.0) | ND |
| GLY.PRO.MNA | 0 (pH 8.0) | 2 (pH 8.0) | ND | 0 (pH 8.0) |
| Z-PRO.NAM | ND | 0 (pH 8.0) | 0 (E, pH 5.0–8.0) | ND |
| HYDROXYPRO. NAM | ND | 2 (pH 5.0) | ND | 0 (pH 5.0) |
| ARG.NAM | ND | A (pH 8.0); 0 (pH 5) | 2 (D, pH 8) | ND |
| Z-ARG.PRO.NAM | ND | 2 | 2 (D, pH 8) | ND |
| T-boc.VAL. LEU.LYS.AMC | ND | ND | 2 | ND |

TABLE 8

| CONJUGATES | PRONASE (VENDOR 1) FAST GARNET COLOR SCORE (pH) | PRONASE (VENDOR 2) FAST GARNET GBC (pH) COLOR SCORE | PROLINE IMINOPEPTIDASE FAST GARNET COLOR SCORE (pH) |
|---|---|---|---|
| PRO.NAM | 1.5 (pH 8.0) | 2 (pH 8.0) | 2 (pH 8.0) |
| PRO.METHOXY.NAM | ND | ND | 2 (pH 8.0) 2 (pH 5.0) |
| GLY.PRO.MNA | 0 (pH 8.0) | 0 (pH 8.0) | 0 (pH 8.0) |
| Z-PRO.NAM | ND | ND | ND |
| HYDROXYPRO.NAM | ND | ND | 2 (pH 8.0) 2 (pH 5.0) |
| ARG.NAM | ND | ND | ND |
| Z.ARG.PRO.NAM | ND | ND | ND |
| T-boc. VAL.LEU.LYS.AMC | ND | ND | ND |

D. INTERPRETATION

The *Mobiluncus curtisii* ATCC strain 35241 cells tested contained one or more cell-bound enzymes capable of hydrolyzing the following conjugates: L-prolyl-beta-naphthylamide; L-glycyl-L-prolyl-4-methoxy-naphthylamide; L-hydroxyprolyl-beta-naphthylamide; L-arginyl-beta-naphthylamide; Z-L-arginyl.L-prolyl-beta-naphthylamide; and, T-boc-L-valyl.L-leucyl.L-lysyl-7-amino-4-methyl coumarin. Reporter groups were released upon enzymatic hydrolysis of these conjugates, and were detected either in a dried chromogenic indicator lamina containing Fast Garnet GBC or with a liquid system containing PDMAC. The *Mobiluncus curtisii* ATCC strain 35241 cells tested lacked the enzymes needed to hydrolyze the conjugates L-prolyl-4-methoxynaphthylamide or Z-L-prolyl-beta-naphthylamide. With these conjugates, free reporter groups were not released, and no color formed either in the chromogenic indicator laminae or in the chromogenic liquid reagent solutions.

Like *Mobiluncus curtisii* ATCC strain 35241, the *Mobiluncus mullieris* ATCC strain 35239 cells contained an enzyme capable of hydrolyzing the conjugate, L-prolyl-beta-naphthylamide, and thereby releasing the reporter group, beta-naphthylamide, which was detectable with Fast Garnet GBC indicator laminae. Unlike *Mobiluncus curtisii* ATCC strain 35241, *Mobiluncus mullieris* ATCC strain 35239 cells lacked the enzymatic capacity needed to hydrolyze the conjugate, L-glycyl-L-prolyl-4-methoxynaphthylamide, at pH 8.0. If desired, this differential hydrolytic capacity could be used to make tests which would detect either both species of Mobiluncus (i.e., PRO.NAM), or to distinguish between them (i.e., GLY.PRO.NAM).

The *Candida albicans* ATCC strain 28366 cells tested hydrolyzed the conjugate, L-prolyl-beta-naphthylamide. Hydrolysis of L-prolyl-beta-naphthylamide by *C. albicans* ATCC strain 28366 cells was considerably slower than that by *Mobiluncus curtisii* ATCC strain 35241 and *Mobiluncus mullieris* ATCC strain 35237 cells. Unlike *Mobiluncus curtisii* ATCC strain 35241 cells, *C. albicans* ATCC strain 28366 cells lacked the capacity to hydrolyze the conjugates, hydroxy-L-prolyl-beta-naphthylamide and L-glycyl-L-prolyl-4-methoxynaphthylamide. This differential enzymatic capacity could be used to make tests employing selective conjugates (e.g., L-prolyl-beta-naphthylamide), which would either detect both species of Mobiluncus, or selectively detect *Mobiluncus curtisii* ATCC strain 35241 cells in the presence of *Candida albicans* ATCC strain 28366 and *Mobiluncus mullieris* ATCC strain 35239 cells (L-gly.L-pro-4-methoxynaphthylamide).

Purified pronase preparations from two separate vendors and purified proline iminopeptidase from *Bacillus coagu-*

*lans* hydrolyzed the conjugates L-prolyl-beta-naphthylamide, thereby releasing the free reporter group, 2-naphthylamine which reacted with Fast Garnet GBC indicator laminae to produce a color. The purified *B. coagulans* proline iminopeptidase also released 4-methoxy naphthylamide from L-prolyl-beta-methoxynaphthylamide and beta-naphthylamine from hydroxy-L-prolyl-beta-naphthylamide, thereby producing a red color. Therefore, all of these enzymes could be used as positive enzyme controls for proline iminopeptidase activity tests where L-prolyl-beta-naphthylamide is the conjugate, and Fast Garnet GBC is the indicator. However, only the *B. coagulans* enzyme could be used as a positive control in test methods which employed L-prolyl-4-methoxynaphthylamide or hydroxy-L-prolyl-4-methoxynaphthylamide as conjugates. Also note that purified prolineaminopeptidase from *B. coagulans* hydrolyzes PRO.METHOXY.NAM but the *M. curtisii* cell do not. Hence to the extent that this *B. coagulans* enzyme represents a bacterial proline iminopeptidase, it differs from the Mobilincus enzyme or enzymes. This suggests that the purified *B. coagulans* prolineaminopeptidase enzyme may be one which only exhibits prolineaminopeptidase activity.

EXPERIMENT V

This experiment tested vaginal fluid specimens from normal, uninfected women, and women with vulvovaginal candidiasis for proline iminopeptidase activity using dried Fast Garnet GBC chromogenic indicator laminae, and L-prolyl-beta-naphthylamide solution as the conjugate.

A. MATERIALS:
1. Fast Garnet GBC chromogenic indicator laminae prepared as described in PREPARATION A (#20 Meyer rod).
2. standard dacron clinical swabs containing undiluted vaginal fluid samples from women diagnosed as follows:
   a. normal (i.e., not having any form of infectious vaginitis); or,
   b. infected with vulvovaginal candidiasis, but not bacterial vaginosis. The swabs were frozen at −70° C. until tested.
3. conjugate solution, 10 mM L-prolyl-beta-naphthylamide (PRO.NAM), in water.

B. PROCEDURES

The swabs containing vaginal fluid were thawed and the fluid was removed from each clinical swab by centrifugation. 20 µL aliquots of vaginal fluid from each specimen was added to test tubes containing 5 µL PRO.NAM. The mixture was allowed to incubate for 10 minutes at room temperature, and a 20 µL aliquot was removed from each incubation mixture and added to a Fast Garnet GBC indicator lamina. After 10 minutes, color formation was noted on the Fast Garnet GBC indicator laminae.

TABLE 9

| COLOR SCORE: | INTERPRETATION |
| --- | --- |
| 0 | no red color formation |
| 0.25 | faintest red color detectable visually |
| 0.5 | distinct red color |
| 1.0 | red color between 1.0 and 2.0 in intensity |
| 2.0 | darkest red color possible in test system |

C. RESULTS

No color formation was generated in the Fast Garnet GBC chromogenic indicator laminae by any of the vaginal fluid specimens from either patient population.

TABLE 10

| SPECIMEN NUMBER | CLINICAL DIAGNOSIS | SAMPLE VOLUME (µL) | 10 mM PRO.NAM VOLUME (µL) | COLOR SCORE |
| --- | --- | --- | --- | --- |
| 1 | normal | 20 | 5 | 0 |
| 2 | normal | 20 | 5 | 0 |
| 3 | normal | 20 | 5 | 0 |
| 4 | candidiasis | 20 | 5 | 0 |
| 5 | candidiasis | 20 | 5 | 0 |
| 6 | candidiasis | 20 | 5 | 0 |
| 7 | candidiasis | 20 | 5 | 0 |
| 8 | candidiasis | 20 | 5 | 0 |

D. INTERPRETATION

Vaginal fluid from normal women lacked sufficient proline iminopeptidase activity under the conditions of the assay to hydrolyze the conjugate, PRO.NAM, and failed to release the reporter group, beta-naphthylamine. Since no beta-naphthylamine was released, no color formation occurred in the Fast Garnet GBC chromogenic indicator laminae. The same can be said of vaginal fluid from women with clinically diagnosed symptomatic vulvovaginal candidiasis. Based on these results, vaginal fluid from normal women, or women with symptomatic vulvovaginal candidiasis alone would not be expected to produce a positive test result in a positive test for proline iminopeptidase activity under the reaction conditions defined above.

EXPERIMENT VI

This experiment tests the ability of proline iminopeptidase activity test devices employing dried laminae containing L-prolyl-beta-naphthylamide as the hydrolyzable conjugate for proline iminopeptidase activity and Fast Garnet GBC chromogenic indicator laminae to detect proline iminopeptidase activity in vaginal fluid specimens from uninfected women, women with Bacterial Vaginosis and women with other forms of infectious vaginitis.

A. MATERIALS
1. 266 undiluted vaginal fluid samples:
   a. 39 samples from women diagnostically uninfected women
   b. 32 samples from women with diagnostically proven bacterial vaginosis, but no other form of infectious vaginitis
   c. 28 specimens from women with diagnostically proven bacterial vaginosis and at least one additional vaginal infection
   d. 167 specimens women with diagnostically proven vaginal or cervical infections, but not including bacterial vaginosis.

The specimens were obtained on dacron clinical swabs and frozen and stored at −70° C. until tested. For testing, the swabs were thawed and centrifuged to extract the vaginal fluid. The swabs were discarded, the undiluted vaginal fluid was immediately resuspended and used in the devices as outlined below.

2. proline iminopeptidase test devices made as described in PREPARATION C.

B. PROCEDURES

Vaginal fluid specimens removed from the clinical swabs were vortexed to resuspend any particulate matter in the undiluted supernatant vaginal fluid, and was added to the test devices with a volumetric micropipette. After 5 minutes at room temperature, the devices were examined for the formation of a red color.

TABLE 11

| COLOR SCORE: | INTERPRETATION |
|---|---|
| 0 | no red color formation |
| 0.25 | faintest red color detectable visually |
| 0.5 | distinct red color |
| 1.0 | red color between 1.0 and 2.0 in intensity |
| 2.0 | darkest red color possible in test system |

C. RESULTS

The vast majority (93%) of vaginal fluid specimens obtained from women with diagnostically proven bacterial vaginosis, alone, or with other forms of vaginal infectious vaginitis produced a distinct red color in five minutes or less. Almost all (94%) vaginal fluid specimens from women without bacterial vaginosis, whether, uninfected, or multiply infected with other agents, failed to produce a red color.

TABLE 12

| | TEST EVALUATION CRITERIA* | | |
|---|---|---|---|
| 1. | SENSITIVITY | = | Number of Correct Test Positives / Total Number of Positive Patients |
| 2. | SPECIFICITY | = | Number of Correct Test Negatives / Total Number of Negative Patients |
| 3. | PREDICTIVE VALUE POSITIVE | = | Number of Correct Test Positives / Total Number of Positive Patients |
| 4. | PREDICTIVE VALUE NEGATIVE | = | Number of Correct Test Positives / Total Number of Negative Patients |
| 5. | EFFICIENCY | = | Number of Correct Positives + Number of Correct Negatives / Total Number of Tests Carried Out |

*From: E. G. Evans, et al., Eur. J. Obstet. Gyn. Reprod. Biol., 1986, 22:365–371

TABLE 13

SOLID PHASE TEST FOR PROLINE IMINO PEPTIDASE EVALUATION OF RESULTS ON CLINICAL SPECIMENS

| | |
|---|---|
| sensitivity | 93.3% |
| specificity | 93.8% |
| predictive value positive | 90.3% |
| predictive value negative | 95.7% |
| efficiency | 93.6% |

D. INTERPRETATION

The process employed to detect vaginal fluid proline iminopeptidase activity in published procedures required sample extraction from swabs with saline, centrifugation, reconstitution, four hour incubation at elevated temperatures, and multiple components and steps. The proline iminopeptidase activity test devices permitted detection of proline iminopeptidase activity, and thereby bacterial vaginosis with excellent sensitivity and specificity in five minutes at room temperature with untreated vaginal fluid specimens and minimal manipulation. The sensitivity, specificity, predictive values and overall efficiency of the devices in detecting bacterial vaginosis are defined and presented above.

EXPERIMENT VII

This experiment tests the ability of four detergents to inhibit *Mobiluncus curtisii* ATCC strain 35241 proline iminopeptidase activity.

A. MATERIALS 1. detergents (10% wt/wt) in distilled water.
   a. sodium dodecyl sulfate.
   b. Sipon ESY.
   c. Neodel 26-3A.
   d. sodium octadecyl sulfate.
2. 10 mM conjugate, L-prolyl-beta-naphthylamide (PRO.NAM).
3. para-dimethylaminocinnamaldehyde liquid chromogenic reagent (PREPARATION E).
4. distilled water.
5. *Mobiluncus curtisii* ATCC strain 35241 cell suspension (PREPARATION G)

B. PROCEDURES

To one set of four test tubes were added 20 μL cell suspension, 5 μL conjugate, and 65 μL distilled water. After 10 minutes incubation at room temperature, 10 μL detergent and 90 μL chromogen solution was added and the color formation noted.

To a second set of four test tubes were added 20 μL cell suspension, 5 μL conjugate, and 65 μL detergent solution. After 10 minutes incubation of these components at room temperature, 10 μL water and 90 μL chromogen solution was added and the color formation noted.

C. RESULTS

A red color formed in the first set of tubes containing only cells and conjugate upon addition of the chromogen solution. No red color formed in the second set of tubes in which the cells and conjugate were incubated with detergent prior to addition of the PDMAC chromogenic indicator.

TABLE 14

| FIRST ADDITIONS (μL) | | | |
|---|---|---|---|
| A CELLS (μL) | B PRO.NAM | C DETERGENT (μL) | D WATER (μL) |
| 20 | 5 | none | 65 |
| 20 | 5 | none | 65 |
| 20 | 5 | none | 65 |
| 20 | 5 | none | 65 |
| 20 | 5 | sodium dodecyl sulfate (10) | 65 |
| 20 | 5 | SIPON ESY (10) | 65 |
| 20 | 5 | NEODEL 25-3A (10) | 65 |
| 20 | 5 | sodium octadecyl sulfate (10) | 65 |

TABLE 15

| SECOND ADDITIONS (AFTER 10 MINUTE INCUBATION) | | |
|---|---|---|
| DETERGENT | CHROMOGEN | COLOR |
| SDS (10) | 90 | red |
| sipon esy (10) | 90 | red |
| neodel 25 - 3a (10) | 90 | red |
| sodium octadecyl sulfate (10) | 90 | red |
| none | 90 | yellow |
| none | 90 | yellow |
| none | 90 | yellow |
| none | 90 | yellow |

D. INTERPRETATION

Red color formed in the first set of tubes because the *Mobiluncus curtisii* ATCC strain 35241 cells contained proline iminopeptidase activity. PRO.NAM was hydrolyzed, releasing the reporter group, beta-naphthylamine, which reacted with the PDMAC chromogenic indicator to change from a yellow color to red. Although detergent was added to this set of test tubes after the 10 minute incubation, hydrolysis of the PRO.NAM had already occurred, and the detergents did not interfere with red color formation.

Red color did not form in the second set of tubes because the proline iminopeptidase enzyme activity of the *Mobiluncus curtisii* ATCC strain 35241 cells was inactivated by the added detergents, which were present throughout the entire incubation period. PRO.NAM was not hydrolyzed, and therefore the reporter group, beta-naphthylamine was not released, and there was no change from a yellow color to red. Hence, any of the detergents added might be employed to inactivate proline iminopeptidase activity of *Mobiluncus curtisii* ATCC strain 35241 cells, and thereby serve as a negative control for a proline iminopeptidase activity-based test where PRO.NAM was employed as the conjugate.

EXPERIMENT VIII

This experiment tests the ability of enzyme inhibitors to inhibit *Mobiluncus curtisii* ATCC strain 35241 hydrolysis of L-prolyl-beta-naphthylamide (proline iminopeptidase activity).

A. MATERIALS

1. Enzyme inhibitors dissolved in solvents indicated:
   a. 100 mM ethyleneglycol-bis-(beta-aminoethyl ether)-N,N,N',N'-tetraacetic acid (EGTA) in water.
   b. 20 mM dithiothreitol (DTT) in water.
   c. 10 mM N-tosyl-L-phenylalanine chloromethyl ketone (TPCK) in dimethylformamide.
   d. 10 mM N-tosyl-L-lysine-chloromethyl ketone (TLCK) in dimethylformamide.
   e. 40 mM N-ethylmaleimide (NEM) in water.
   f. 10 mM pepstatin in ethanol.
   g. 10 mM para-chloromercuribenzoate (PCMB) in water.
   h. 10 mM phenyl methyl sulfonyl fluoride (PMSF) in water.
2. Other materials:
   a. distilled water.
   b. dimethylformamide.
   c. ethanol.
   d. 100 mM Tris buffer, pH 8.0.
   e. *Mobiluncus curtisii* cell suspension (PREPARATION G).
   f. para-dimethylaminocinnamaldehyde indicator (PREPARATION E).
   g. 10 mM conjugate, L-prolyl-beta-naphthylamide in water.

B. PROCEDURES

150 µL cell suspension, 10 µL conjugate, (PRO.NAM), 10 µL inhibitor, and 30 µL buffer were added to test tubes, and the suspension incubated for 1.5 hours at room temperature. 80 µL of the suspension was removed from the incubation tubes and added to 80 µL of the chromogen solution in a second set of tubes and the color formation noted.

TABLE 16

| COLOR SCORE: | INTERPRETATION |
|---|---|
| 0 | no red color formation |
| 0.25 | faintest red color detectable visually |
| 0.5 | distinct red color |
| 1.0 | red color between 1.0 and 2.0 in intensity |
| 2.0 | darkest red color possible in test system |

C. RESULTS

A red color formed in all tubes containing chromogen.

TABLE 17

| INHIBITOR | CONCENTRATION (mM) | TEST COLOR |
|---|---|---|
| water | none | 2 |
| ethanol | 5% vol/vol | 2 |
| DMF | 10% vol/vol | 2 |
| EGTA | 5 | 2 |
| DTT | 1 | 2 |
| TPCK | 0.5 | 2 |
| NEM | 0.5 | 2 |
| PMSF | 2 | 2 |
| pepstatin | 0.5 | 2 |
| PCMB | 0.5 | 2 |

D. INTERPRETATION

Known inhibitors of enzymes, including metallohydrolases (e.g., EGTA), disulfide-requiring hydrolases (e.g., DTT), thiol group-requiring hydrolases (e.g., NEM, PCMB), aspartic hydrolases (e.g., PEPSTATIN), and serine hydrolases (e.g., TCPK, TLCK, and PMSF) did not inhibit the proline iminopeptidase activity of *Mobiluncus curtisii* ATCC strain 35241 cells. Hence, these classes of hydrolase inhibitors can be incorporated into test reagents, test methods or test devices designed to detect proline iminopeptidase activity, and thereby minimize interference from other types of hydrolases, and increase specificity for proline iminopeptidase.

EXPERIMENT X

This experiment tests the ability of enzyme inhibitors to inhibit *Mobiluncus curtisii* ATCC strain 35241 cell hydrolysis of Z-L-arg.L-arg.AFC and t-boc-L-val.L-leu.L-lys.7-amino-4-methyl coumarin.

A. MATERIALS

1. Enzyme inhibitors dissolved in solvents indicated:
   a. 200 mM ethyleneglycol-bis-aminoethyl ether)-N,N,N',N'-tetraacetic acid (EGTA) in water.
   b. 20 mM dithiothreitol (DTT) in water.
   c. 10 mM N-tosyl-L-phenylalanine chloromethyl ketone (TPCK) in dimethylformamide.
   d. 10 mM N-tosyl-L-lysine-chloromethyl ketone (TLCK) in dimethylformamide.

e. 40 mM N-ethylmaleimide (NEM) in water.

f. 10 mM pepstatin in ethanol.

g. 10 mM para-chloromercuribenzoate (PCMB) in water.

h. 10 mM phenyl methyl sulfonyl fluoride (PMSF) in water.

2. Other materials:

a. distilled water.

b. dimethylformamide.

c. ethanol.

d. 100 mM Tris buffer, pH 8.0.

e. *Mobiluncus curtisii* ATCC strain 35241 cell suspension (PREPARATION G).

f. para-dimethylaminocinnamaldehyde indicator (PREPARATION E).

g. 10 mM conjugate, Z-ARG.ARG.AFC, in dimethylformamide (DMF).

h. 10 mM conjugate, t-boc-VAL.LEU.LYS.AFC, in dimethylformamide (DMF).

B. PROCEDURES

50 μL cell suspension, 5 μL conjugate, 10 μL inhibitor, and 35 μL buffer were added to test tubes, and the suspension incubated for 1.5 hours at room temperature. 90 μL of the incubated suspension was added to 90 μL of the chromogen solution and the color formation noted.

TABLE 18

| COLOR SCORE: | INTERPRETATION |
| --- | --- |
| 0 | no red color formation |
| 0.25 | faintest red color detectable visually |
| 0.5 | distinct red color |
| 1.0 | red color between 1.0 and 2.0 in intensity |
| 2.0 | darkest red color possible in test system |

C. RESULTS (Z-ARG.ARG.AFC as the conjugate)

A red color formed in all the tubes treated with water, ethanol, DMF, EGTA, DTT, PMSF, pepstatin and NEM. Very little color formed in the tubes containing TPCK, or TLCK.

TABLE 19

| INHIBITOR | CONCENTRATION (Mm) | TEST COLOR |
| --- | --- | --- |
| water | none | 2 |
| ethanol | 5% vol/vol | 2 |
| DMF | 5% vol/vol | 2 |
| EGTA | 5 | 2 |
| DTT | 1 | 2 |
| TPCK | 0.5 | 0.5 |
| TLCK | 0.5 | 0.5 |
| NEM | 2 | 2 |
| PMSF | 0.5 | 2 |
| pepstatin | 0.5 | 2 |

D. INTERPRETATION

*Mobiluncus curtisii* ATCC strain 35241 cells have the enzymatic capacity to hydrolyze the conjugate Z.ARG.ARG.AFC. Small amounts or added water, DMF, or ethanol did not significantly inhibit the ability of the cells to hydrolyze Z.ARG.AFG.AFC. Similarly, EGTA, DTT, PMSF, NEM, and pepstatin had no significant inhibitory effect. However, TPCK and TLCK inhibited hydrolysis almost completely. When compared to the inhibition pattern seen with PRO.NAM as a conjugate (EXPERIMENT VIII), it is clear that different enzymes in *Mobiluncus curtisii* ATCC strain 35241 cells are responsible for hydrolyzing PRO.NAM and Z-ARG.ARG.AFC. These enzymatic activities can be distinguished on the basis of inhibition pattern.

E. RESULTS (t-boc.VAL.LEU.LYS.7-AMC)

The color forming pattern observed was similar to that seen with Z-ARG.ARG.AFC as conjugate.

TABLE 20

| INHIBITOR | CONCENTRATION (Mm) | TEST COLOR |
| --- | --- | --- |
| none | — | 2 |
| EGTA | 5 | 2 |
| DTT | 1 | 2 |
| TPCK | 0.5 | 0 |
| TLCK | 0.5 | 0 |
| NEM | 2 | 2 |
| PMSF | 0.5 | 1 |
| pepstatin | 0.5 | 2 |
| DMF | 5% vol/vol | 2 |
| ethanol | 5% vol/vol | 2 |

F. INTERPRETATION

*Mobiluncus curtisii* ATCC strain 35241 cells have the enzymatic capacity to hydrolyze the conjugate T-boc-VAL.LEU.LYS.7-AMC. Small amounts of water, DMF, or ethanol added to the incubation mixtures did not significantly inhibit the ability of the cells to hydrolyze T-boc-VAL.LEU.LYS.AMC. Similarly, EGTA, DTT, NEM and pepstatin had no significant inhibitory effect. PMSF inhibited activity approximately 50%. However, TPCK and TLCK essentially inhibited hydrolysis completely. This hydrolysis and inhibition pattern was essentially the same as that seen with Z-ARG.ARG.AFC, suggesting that the same enzyme or very similar enzymes are used to hydrolyze both conjugates. It would be difficult to distinguish between these enzymes using the inhibitors tested.

However, when compared to the inhibition pattern seen with PRO.NAM as a conjugate (EXPERIMENT VIII), it is clear that at least two different enzymes are responsible for hydrolyzing PRO.NAM and the other two conjugates. These enzymes can be distinguished on the basis of inhibition pattern.

EXPERIMENT XI

This experiment tests the ability of metal ions to inhibit *Mobiluncus curtisii* ATCC strain 35241 cell hydrolysis of the conjugate, L-prolyl-beta-naphthylamide.

A. MATERIALS

1. Metal salts dissolved in water:

a. 100 mM $HgCl_2$.

b. 100 mM $CuCl_2$.

c. 100 mM $CrCl_2$.

d. 100 mM $ZnCl_2$.

e. 100 mM $CaCl_2$.

f. 100 mM $MgCl_2$.

g. 100 mM $MnCl_2$.

h. 100 mM NaCl.

2. Other materials:

a. distilled water.

b. *Mobiluncus curtisii* ATCC strain 35241 cell suspension (PREPARATION G).

c. 10 mM conjugate, L-prolyl-beta-naphthylamide (PRO.NAM) in water.

d. Fast Garnet GBC chromogenic indicator laminae (#20 Meyer Rod) (PREPARATION A).

B. PROCEDURES

30 μL cell suspension, 10 μL conjugate, PRO.NAM, and 10 μL salt solution or water were added to test tubes, and the suspension incubated for 2 minutes at room temperature. 20 μL of the suspension was removed from the incubation tubes and added to Fast Garnet GBC chromogenic indicator laminae. After 3 minutes, the Fast Garnet GBC indicator laminae were examined for a red color.

TABLE 21

| COLOR SCORE: | INTERPRETATION |
|---|---|
| 0 | no red color formation |
| 0.25 | faintest red color detectable visually |
| 0.5 | distinct red color |
| 1.0 | red color between 1.0 and 2.0 in intensity |
| 2.0 | darkest red color possible in test system |
| ND | not done |

C. RESULTS

A dark red spot formed when the suspension of *Mobiluncus curtisii* ATCC strain 35241 cells, conjugate, PRO.NAM, and metal salt solutions were incubated on the Fast Garnet GBC chromogenic indicator laminae, except for those suspensions containing mercuric chloride and cupric chloride. When either of these two metal salts were present, no red color formed.

TABLE 22

| METAL ION | CONCENTRATION (mM) | TEST COLOR |
|---|---|---|
| water | none | 2 |
| $HgCl_2$ | 1 | 0 |
| $CuCl_2$ | 5 | 0 |
| $CrCl_2$ | 20 | 2 |
| $ZnCl_2$ | 20 | 2 |
| $CaCl_2$ | 20 | 2 |
| $MgCl_2$ | 20 | 2 |
| $MnCl_2$ | 20 | 2 |
| NaCl | 20 | 2 |

D. INTERPRETATION

The chloride salts of chromium, zinc, calcium, magnesium, manganese, and sodium did not inhibit the proline iminopeptidase activity of *Mobiluncus curtisii* ATCC strain 35241 cells. Hence, beta-naphthylamine was released from the conjugate, L-prolyl-beta-naphthylamide, and a red color formed on the East Garnet GBC chromogenic indicator laminae. Therefore, these salts can be incorporated into proline iminopeptidase activity test reagents or devices to minimize interference from other types of hydrolases, thereby increasing specificity for proline iminopeptidase activity.

Alternatively, because mercuric and cupric chlorides inhibited the proline iminopeptidase activity of *Mobiluncus curtisii* ATCC strain 35241 cells, they can be incorporated into test systems or devices as a negative control for this activity.

EXPERIMENT XII

This experiment tests the ability of metal ions to inhibit *Mobiluncus curtisii* ATCC strain 35241 hydrolysis of the conjugate, L-arginyl-beta-naphthylamide (ARG.NAM).

A. MATERIALS

1. Metal salts dissolved in water:
   a. 100 mM $HgCl_2$.
   b. 50 mM $CuCl_2$.
   c. 100 mM $CrCl_2$.
   d. 50 mM $ZnCl_2$.
   e. 50 mM $CaCl_2$.
   f. 50 mM $MgCl_2$.
   g. 100 mM $MnCl_2$.
   h. 200 mM NaCl.
   i. 50 mM $CoCl_2$
2. Other materials:
   a. 350 mM Tris buffer, pH 8.0.
   b. distilled water.
   c. *Mobiluncus curtisii* ATCC strain 35241 cell suspension (PREPARATION G).
   d. PDMAC (high buffer capacity, PREPARATION D)
   e. 10 mM conjugate, L-arginyl-beta-naphthylamide (ARG.NAM) in water

B. PROCEDURES

20 μL cell suspension, 50 μL water, 10 μL salt solution, 10 μL buffer, and 5 μL conjugate, ARG.NAM, were added to test tubes, and the suspension incubated for 1 hour at room temperature. 100 μL of the PDMAC chromogen reagent was added, and red color formation after 5 minutes was noted.

TABLE 23

| COLOR SCORE: | INTERPRETATION |
|---|---|
| 0 | no red color formation |
| 0.25 | faintest red color detectable visually |
| 0.5 | distinct red color |
| 1.0 | red color between 1.0 and 2.0 in intensity |
| 2.0 | darkest red color possible in test system |
| ND | not done |

C. RESULTS

A dark red color formed when the suspension of *Mobiluncus curtisii* ATCC strain 35241 cells, conjugate, ARG.NAM, and water or chloride salts of sodium and calcium were exposed to the PDMAC reagent. No color formation was seen in the tube containing 5 mM cupric chloride, and significantly less color was seen in the tube containing 1 mM cupric chloride. Significantly less color was also seen in the tubes containing chlorides of zinc, manganese and cobalt.

TABLE 24

| METAL ION | CONCENTRATION (mM) | TEST COLOR |
|---|---|---|
| water | none | 2 |
| $HgCl_2$ | ND | ND |
| $CuCl_2$ | 5 | 0 |
| $CuCl_2$ | 1 | 1 |
| $ZnCl_2$ | 5 | 0.5 |
| $ZnCl_2$ | 1 | 1 |
| $CaCl_2$ | 5 | 2 |
| $CoCl_2$ | 2.5 | 1 |
| $MnCl_2$ | 5 | 1 |
| NaCl | 10 | 2 |

D. INTERPRETATION

Of the salts tested, chlorides of calcium and sodium did not inhibit the ability of *Mobiluncus curtisii* ATCC strain 35241 cells to hydrolyze the conjugate, L-arginyl-beta-naphthylamide. Hence, the reporter group, beta-naphthylamine was released, and a red color formed after addition of the PDMAC reagent.

Alternatively, 5 mM cupric chloride inhibited the ability of *Mobiluncus curtisii* ATCC strain 35241 cells to catalyze hydrolysis of the conjugate, L-arginyl-beta-naphthylamide, thereby preventing release of the reporter group, beta-naphthylamine, and hence subsequent color formation. Copper salts can be incorporated into test systems or devices as a negative control for this enzyme, under the conditions studied. The inhibition of hydrolysis by the other salts suggest that hydrolysis of the conjugate, L-arginyl-beta-naphthylamide, is catalyzed by different enzymes from the enzyme which catalyzes hydrolysis of the conjugate, L-prolyl-beta-naphthylamide (EXPERIMENT XI). The effect of Zinc and Manganese salts is examined further in EXPERIMENT XIII.

EXPERIMENT XIII

This experiment tests the ability of manganese and zinc chlorides to inhibit *Mobiluncus curtisii* ATCC strain 35241 hydrolysis of the conjugate, L-prolyl-beta-naphthylamide, and the conjugate, L-arginyl-beta-naphthylamide at high and low pH.

A. MATERIALS
1. Metal salts dissolved in water:
   a. 100 mM $ZnCl_2$.
   b. 100 mM $MnCl_2$.
   c. 350 mM Tris buffer, pH 8.0.
   d. 200 mM acetate buffer, pH 5.5
2. Other materials:
   a. distilled water.
   b. *Mobiluncus curtisii* ATCC strain 35241 cell suspension (PREPARATION G).
   c. Fast Garnet GBC chromogenic indicator laminae (#20 Meyer Rod, Procedure A).
   d. 10 mM solutions of L-prolyl-beta-naphthylamide (PRO.NAM) and L-arginyl-beta-naphthylamide (ARG.NAM).

B. PROCEDURES

20 µL cell suspension, 40 µL water, 10 µL salt solution, and 10 µL conjugate solutions (PRO.NAM or ARG.NAM) were added to test tubes, and mixed thoroughly. Immediately thereafter, 20 µL aliquots were removed from each tube, and added directly to Fast Garnet GBC chromogenic indicator laminae. After 5 minutes at room temperature, the Fast Garnet GBC sheets were examined for the formation of a red color.

TABLE 25

| COLOR SCORE: | INTERPRETATION |
|---|---|
| 0 | no red color formation |
| 0.25 | faintest red color detectable visually |
| 0.5 | distinct red color |
| 1.0 | red color between 1.0 and 2.0 In intensity |
| 2.0 | darkest red color possible in test system |
| ND | not done |

C. RESULTS

A red color formed on Fast Garnet 3GBC chromogenic indicator laminae when the suspension of *Mobiluncus curtisii* ATCC strain 35241 cells were incubated with either of the two conjugates at pH 8.0, in the absence of added metal salts.

The most intense red color was seen with PRO.NAM as the conjugate, and at pH 5. With PRO.NAM as the conjugate, less color was seen at pH 8.0. Neither zinc chloride nor manganese chloride affected color formation with the PRO.NAM conjugate at either pH.

With ARG.NAM, as the conjugate, a red color was seen at only at pH 8.0, and then only in the absence of added metal salts. At pH 5.0, no red color formed with ARG.NAM as the conjugate.

TABLE 26

| M. CURTISII | PRO.NAM 2.5 mM | ARG.NAM 2.5 mM | $MnCl_2$ 100 mM | $ZnCl_2$ 100 mM | BUFFER | WATER | COLOR SCORE 5 MINUTES |
|---|---|---|---|---|---|---|---|
| 20 | 10 | 0 | 0 | 0 | 20 µL pH 8 | 50 | 0.5 |
| 20 | 10 | 0 | 10 | 0 | 20 µL pH 8 | 40 | 0.5 |
| 20 | 10 | 0 | 0 | 10 | 20 µL pH 8 | 40 | 0.5 |
| 20 | 10 | 0 | 0 | 0 | 10 µL pH 5 | 50 | 1 |
| 20 | 10 | 0 | 10 | 0 | 10 µL pH 5 | 40 | 1 |
| 20 | 10 | 0 | 0 | 10 | 10 µL pH 5 | 40 | 1 |
| 20 | 0 | 10 | 0 | 0 | 20 µL pH 8 | 50 | 0.5 |
| 20 | 0 | 10 | 10 | 0 | 20 µL pH 8 | 40 | 0 |
| 20 | 0 | 10 | 0 | 10 | 20 µL pH 8 | 40 | 0 |
| 20 | 0 | 10 | 0 | 0 | 10 µL pH 5 | 50 | 0 |
| 20 | 0 | 10 | 10 | 0 | 10 µL pH 5 | 40 | 0 |
| 20 | 0 | 10 | 0 | 10 | 10 µL pH 5 | 40 | 0 |

D. INTERPRETATION

1. *Mobiluncus curtisii* ATCC strain 35241 cells hydrolyzed the conjugate, PRO.NAM thereby releasing the reporter group, beta-naphthylamine. The reporter, beta naphthylamine, group reacted with the Fast Garnet GBC chromogenic indicator laminae to form a red color. The *Mobiluncus curtisii* ATCC strain 35241 enzyme catalyzing this hydrolysis is more efficient at pH 5.0 than at pH 8.0, and a more intense color formed at pH 5.0.

2. Neither zinc chloride nor manganese chloride inhibited the *Mobiluncus curtisii* ATCC strain 35241 enzyme which hydrolyzed the conjugate for proline iminopeptidase, PRO.NAM.

3. At pH 8.0, but not at pH 5.0, *Mobiluncus curtisii* ATCC strain 35241 cells hydrolyzed the conjugate, ARG.NAM, thereby releasing the reporter group, beta-naphthylamine. The reporter group, beta-naphthylamine, reacted with the Fast Garnet GBC chromogenic indicator laminae to form a red color. The *Mobiluncus curtisii* ATCC strain 35241 enzyme catalyzing this hydrolysis functioned over the time interval studied, at pH 8.0, but not at pH 5.0.

4. Both zinc chloride and manganese chloride inhibited the *Mobiluncus curtisii* ATCC strain 35241 enzyme which hydrolyzed the conjugate, ARG.NAM at pH 8.0.

5. The demonstrated differences in pH profile, and the differing responses to zinc chloride and manganese chloride indicate that the conjugates, PRO.NAM and ARG.NAM are hydrolyzed by different enzymes which are distinguishable on the basis of pH profile and inhibition by metal salts.

EXPERIMENT XIV

This experiment was designed to identify the capacity of naphthalene derivatives to react with Fast Garnet GBC chromogenic inhibitor laminae, and thereby serve as positive control elements capable of testing the performance of the Fast Garnet GBC chromogenic indicator laminae.

A. MATERIALS
1. Fast Garnet GBC chromogenic indicator laminae (PROCEDURE A).
2. 2-naphthylamine.
3. 1-naphthylamine.
4. 3-amino-2-naphthoic acid.
5. 3-amino-2-naphthoyl-L-aspartic acid.
6. 4-methoxy-2-naphthylamine.
7. 6-amino naphthol-3-sulfonic acid.
8. 8-amino-2,7-naphthalene disulfonic acid.
9. 2-amino-1-naphthalene sulfonic acid.
10. 2-amino-3,6,-naphthalene disulfonic acid.
11. 6-amino-naphthalene sulfonic acid.
12. 7-amino-1,3-naphthalene disulfonic acid.
13. 3-amino-2,7-naphthalene disulfonic acid.
14. 10% (wt/wt) ethylcellulose solution in methanol.
15. 10% (wt/wt) ethylcellulose solution in ethanol.
16. 1.7M manganese chloride in water.
17. 10% (wt/wt) hydroxypropylcellulose in ethanol.
19. 10% (wt/vol) octyl glucoside in water.
20. 1.6M Tris buffer, pH 8.5.

B. PROCEDURES
1. Preparation of Fast Garnet GBC chromogenic indicator laminae:

3.5 mg Fast Garnet GBC was added to 180 μL ethylcellulose solution in methanol and 720 μL ethylcellulose in ethanol. The mixture was stirred, and 50 μL MnCl$_2$ solution were added. After thorough mixing, the solution was drawn into thin chromogenic indicator laminae on the polyethylene surface of a 7 mil Mylar®:3 mil polyethylene laminate with a #10 Meyer Rod. The indicator laminae were dried with a stream of warm air, and stored sealed in plastic bag until used.

2. Preparation of Naphthalene-derivative laminae:

Sufficient solid naphthalene derivative to prepare a 1 mL 5 mM solution was added to 50 μL water and 50 μL Tris buffer, and mixed until the solid was dissolved. 900 μL hydroxypropylcellulose solution in ethanol was added, and the mixture stirred until homogenous. After thorough mixing, the solution was drawn into thin laminae on the polyethylene surface of a 7 mil Mylar®:3 mil polyethylene laminate with a #10 Meyer Rod. The laminae was dried with a stream of warm air, and stored sealed in plastic bag until used.

3. Preparation of Manually Assembled Test Devices:

Devices were assembled as described in PREPARATION C, with Fast Garnet GBC chromogenic indicator laminae on the inner surface of the top, and the naphthalene derivative laminae on the inner surface of the bottom of the device. Sufficient water was added to the devices to fill the reaction chamber, and the formation of color on the top sheet was noted.

TABLE 27

| COLOR SCORE: | INTERPRETATION |
| --- | --- |
| 0 | no red color formation |
| 0.25 | faintest red color detectable visually |
| 0.5 | distinct red color |
| 1.0 | red color between 1.0 and 2.0 In intensity |
| 2.0 | darkest red color possible in test system |
| ND | not done |

C. RESULTS

Devices containing the following compounds produced a color on the Fast Garnet GBC chromogenic laminae of the device: 2-naphthylamine, 1-naphthylamine, 3-amino-2-naphthoic acid, 3-amino-2-naphthoyl-L-aspartic acid, 4-methoxy-2-naphthylamine, 6-amino naphthol-3-sulfonic acid, 8-amino-2,7-naphthalene disulfonic acid, and 2-amino-1-naphthalene sulfonic acid.

No color formation was seen in the Fast Garnet GBC chromogenic laminae of devices containing the following derivatives: 2-amino-3,6-naphthalene disulfonic acid, 6-amino-naphthalene sulfonic acid, 7-amino-1,3-naphthalene disulfonic acid, and 3-amino-2,7-naphthalene disulfonic acid.

TABLE 28

| COMPOUND | COLOR SCORE |
| --- | --- |
| 2-naphthylamine | 2 |
| 1-naphthylamine | 2 |
| 3-amino-2-naphthoic acid | 2 |
| 3-amino-naphthoyl-1-aspartic acid | 2 |
| 4-methoxy-2-naphthylamine | 2 |
| 6-amino-1-naphthol-3-sulfonic acid | 1.5 |
| 8-amino-2,7-naphthalene disulfonic acid | 0.5 |
| 2-amino-1-naphthalene disulfonic acid | 0.25 |
| 2-amino-3,6,naphthalene disulfonic acid | 0 |
| 6-amino-naphthalene sulfonic acid | 0 |
| 7-amino-1,3-naphthalene disulfonic acid | 0 |
| 3-amino-2,7-naphthalene disulfonic acid | 0 |

D. INTERPRETATION

The compounds which produced a red color on the inner surface of the devices (2-naphthylamine, 1-naphthylamine, 3-amino-2-naphthoic acid, 3-amino-2-naphthoyl-L-aspartic acid, 4-methoxy-2-naphthylamine, 6-amino naphthol-3-sulfonic acid, 8-amino-2,7-naphthalene disulfonic acid, and 2-amino-1-naphthalene sulfonic acid) reacted with the Fast Garnet GBC chromogenic laminae, and could be utilized as a positive control to detect appropriate performance of the Fast Garnet GBC indicator lamina component of the device. Selection of the final derivative would be contingent on factors like commercial availability, cost, stability, rate of solubilization, toxicity, and other considerations known to those skilled in the art.

Not all naphthylamine derivatives, however, would be suitable as positive control elements. Those compounds which failed to produce a red color (2-amino-3,6-naphthalene disulfonic acid, 6-amino-naphthalene sulfonic acid, 7-amino-1,3-naphthalene disulfonic acid, and 3-amino-2,7-naphthalene disulfonic acid) would not function in this capacity.

The foregoing is offered for purposes of illustration. It will be readily apparent to those skilled in the art that the operating conditions, materials, procedural steps and other parameters of the methods and test devices described herein may be further modified or substituted in ways without departing from the spirit and scope of the invention.

What is claimed is:

1. A method for assaying for the presence or absence of an analyte selected from the group consisting of a catalytically active hydrolase and an inhibitor of a catalytically active hydrolase in a sample, said method comprising:
   (a) contacting said sample with a solid-phase conjugate consisting of a reporter group coupled to a substrate residue yet cleavable therefrom by said catalytically active hydrolase, said reporter group when not so coupled being capable of causing a detectable change in an indicator, this step being performed in an environment in which the condition of said reporter group as either coupled or decoupled correlates with the presence or absence of said analyte;
   (b) during or subsequent to step (a), contacting said sample with a solid-phase indicator which undergoes a detectable change upon action of said reporter group; and
   (c) observing whether said indicator undergoes a detectable change, said detectable change being an indication of the presence or absence of said analyte in said sample.

2. A method in accordance with claim 1 wherein said analyte is a catalytically active hydrolase.

3. A method in accordance with claim 2 wherein said analyte is a member selected from the group consisting of hydrolases acting on ester bonds, hydrolases acting on glycoside bonds, hydrolases acting on ether bonds, hydrolases acting on peptide bonds, hydrolases acting on carbon—nitrogen (C—N) bonds other than peptide bonds, hydrolases acting on carbon—carbon (C—C) bonds, hydrolases acting on acid-anhydride bonds, hydrolases acting on halide bonds and hydrolases acting on phosphorous—nitrogen (P—N) bonds.

4. A method in accordance with claim 3 wherein said hydrolase is a hydrolase acting on peptide bonds selected from the group consisting of α-amino-acyl-peptide hydrolases, peptidyl-amino-acid hydrolases, dipeptide hydrolases and peptidyl-peptide hydrolases.

5. A method in accordance with claim 4 wherein said hydrolase is one which exhibits proline iminopeptidase activity.

6. A method in accordance with claim 1 wherein said reporter group is a member selected from the group consisting of phenols, naphthols, aromatic amines and amino acids.

7. A method in accordance with claim 1 wherein said substrate residue is a member selected from the group consisting of amino acids, peptides, monosaccharides, disaccharides, nucleotides, carboxylic acids and alcohols.

8. A method in accordance with claim 1 wherein said solid-phase indicator is a visual indicator.

9. A method in accordance with claim 8 wherein said visual indicator is a chromogenic indicator selected from the group consisting of diazonium salts and tetrazonium salts.

10. A method in accordance with claim 9 wherein said chromogenic indicator is a diazonium salt selected from the group consisting of Fast Garnet GBC, Fast Dark Blue G, Fast Red B, Fast Corinth V, Fast Bordeaux and Fast Black K.

11. A method in accordance with claim 8 wherein said visual indicator is a chromogenic indicator consisting of an amino acid oxidase; a chromogen selected from the group consisting of guaiac, 2,2'-azino-bis(3-ethyl-benzthiazoline-6-sulfonic acid), tetramethylbenzidine, phenol, 4-aminoantipyrine and 4,5-dihydroxynaphthalene; a redox catalyst selected from the group consisting of peroxidases, iron protoporphyrin and metal ions; and oxygen.

12. A method in accordance with claim 1 wherein said solid-phase indicator is immobilized on a solid support.

13. A method in accordance with claim 1 wherein said solid-phase conjugate and said solid-phase indicator are each deposited on a solid support.

14. A method in accordance with claim 1 wherein said solid-phase conjugate and said solid-phase indicator are both deposited on a common surface of a solid support in a preselected geometric pattern.

15. A method in accordance with claim 1 wherein said solid-phase conjugate and said solid-phase indicator are each immobilized on a solid support.

16. A method in accordance with claim 1 wherein (a) further comprises contacting said sample with an interference hydrolase inhibitor selected to inhibit the activity of any hydrolases other than said analyte.

17. A method in accordance with claim 1 wherein said solid-phase conjugate and said solid-phase indicator are immobilized on first and second solid supports, respectively, and said method comprises contacting said sample with said first and second solid-phase supports simultaneously.

18. A method in accordance with claim 1 wherein said analyte is an enzyme exhibiting proline iminopeptidase activity, said solid-phase conjugate is a member selected from the group consisting of L-prolyl-beta-naphthylamide, hydroxy-L-prolyl-beta-naphthylamide and L-prolyl-beta-methoxynaphthylamide, deposited on a first solid support, and said solid-phase indicator is Fast Garnet GBC immobilized on a second solid support.

19. A method in accordance with claim 1 wherein said analyte is an inhibitor of a target hydrolase in a sample, and in which step (a) comprises contacting said sample with said target hydrolase and said solid-phase conjugate.

20. A test device for assaying for the presence of a catalytically active hydrolase in a sample, said test device comprising:
   a receptacle defined at least in part by first and second opposing walls having interior-facing surfaces with a gap therebetween, said first wall, said second wall, or both being of light-transmitting material;
   a solid-phase conjugate deposited on said interior-facing surface of one of said first and second walls, said conjugate consisting of a reporter group coupled to a substrate residue yet cleavable therefrom upon contact with said catalytically active hydrolase, said reporter group when not so coupled being capable of causing a detectable change in an indicator;
   a solid-phase indicator deposited on said interior-facing surface of one of said first and second walls, said indicator being one which undergoes a detectable change upon action of said reporter group; and
   an opening in said receptacle for introduction of said sample.

21. A test device in accordance with claim 20 wherein said solid-phase conjugate is deposited on said interior-facing surface of said first wall, and said solid-phase indicator is deposited on said interior-facing surface of said second wall.

22. A test device in accordance with claim 20 wherein said solid-phase indicator is immobilized on said interior-facing surface of one of said first and second walls.

23. A test device in accordance with claim 20 wherein said solid-phase conjugate is immobilized on said interior-facing surface of said first wall, and said solid-phase indicator is immobilized on said interior-facing surface of said second wall.

24. A test device in accordance with claim 20 wherein said solid-phase indicator is immobilized on said interior-facing surface of said first wall and said opening is in said first wall.

25. A test device in accordance with claim 20 further comprising a positive control species contained in a solid layer on a portion of the interior-facing surface of one of said first and second walls, said positive control species selected such that, when contacted by said sample, said positive control species causes said indicator to undergo a detectable change independently of the presence or absence of said catalytically active hydrolase in said sample.

26. A test device in accordance with claim 25 wherein a detectable change in said indicator in said positive control is an indication that said test device has been filled with said sample.

27. A test device in accordance with claim 20 further comprising a negative control species contained in a solid layer on a portion of the interior-facing surface of one of said first and second walls, said negative control species selected such that, when contacted by said sample, said negative control species prevents said indicator from undergoing a detectable change independently of the presence or absence of said catalytically active hydrolase in said sample.

28. A test device in accordance with claim 20 further comprising:
a positive control species contained in a solid layer on a portion of the interior-facing surface of one of said first and second walls, said positive control species selected such that, when contacted by said sample, said positive control species causes said indicator to undergo a detectable change independently of the presence or absence of said catalytically active hydrolase in said sample; and
a negative control species contained in a solid layer on a portion of the interior-facing surface of one of said first and second walls, said negative control species selected such that, when contacted by said sample, said negative control species prevents said indicator from undergoing a detectable change independently of the presence or absence of said catalytically active hydrolase in said sample.

29. A test device in accordance with claim 20 in which said conjugate comprises a reporter group coupled to a substrate residue and cleavable therefrom upon contact with enzymatically active proline iminopeptidase, said test device thereby being adapted for testing for the presence of bacterial vaginosis by assaying for the presence of proline iminopeptidase activity.

30. A test device in accordance with claim 29 wherein said reporter group is selected from the group consisting of phenols, naphthols, aromatic amines and amino acids.

31. A test device in accordance with claim 29 wherein said substrate residue is selected from the group consisting of L-proline and hydroxy-L-proline.

32. A test device in accordance with claim 29 wherein said indicator is a chromogenic indicator selected from the group consisting of diazonium salts and tetrazonium salts.

33. A test device in accordance with claim 29 wherein said indicator is a member selected from the group consisting of an amino acid oxidase, guaiac, 2,2'-azino-bis(3-ethyl-benzthiazoline-6-sulfonic acid), tetramethylbenzidine, phenol, 4-aminoantipyrine, 4,5-dihydroxynaphthalene, peroxidases, iron protoporphyrin, metal ions, and oxygen.

34. A test device in accordance with claim 20 further comprising a target hydrolase deposited on said interior-facing surface of one of said first and second walls, said target hydrolase being susceptible to inactivation by the presence of an inhibitor, said test device thereby being adapted for testing for the presence of said inhibitor in said sample.

35. A test device for assaying for the presence of an analyte in a sample, said test device comprising:
a penetrable solid support defined at least in part by upper and lower surfaces;
a reagent contained in a solid layer on one of said upper and lower surfaces of said penetrable solid support, said reagent being one which induces a chemical reaction in an indicator when said analyte is present in said sample; and
an indicator contained in a solid layer on the other of said upper and lower surfaces of said penetrable solid support in a manner such that said indicator is separated from said reagent until said sample is added, said indicator being one which undergoes a detectable change upon the occurrence of said chemical reaction.

36. A test device in accordance with claim 35 further comprising a positive control species contained in a solid layer on a portion of one of said upper and lower surfaces of said penetrable solid support, said positive control species selected such that, when contacted by said sample, said positive control species causes said indicator to undergo a detectable change independently of the presence or absence of said analyte in said sample.

37. A test device in accordance with claim 35 further comprising a negative control species contained in a solid layer on a portion of one of said upper and lower surfaces of said penetrable solid support, said negative control species selected such that, when contacted by said sample, said negative control species prevents said indicator from undergoing a detectable change independently of the presence or absence of said analyte in said sample.

38. A test device in accordance with claim 35 further comprising:
a positive control species contained in a solid layer on a portion of one of said upper and lower surfaces of said penetrable solid support, said positive control species selected such that, when contacted by said sample, said positive control species causes said indicator to undergo a detectable change independently of the presence or absence of said analyte in said sample; and
a negative control species contained in a solid layer on a portion of one of said upper and lower surfaces of said penetrable solid support, said negative control species selected such that, when contacted by said sample, said negative control species prevents said indicator from undergoing a detectable change independently of the presence or absence of said analyte in said sample.

39. A test device in accordance with claim 35 wherein said penetrable solid support is contained in a receptacle defined at least in part by first and second opposing walls, said receptacle having an opening for introduction of said sample.

40. A test device in accordance with claim 39 wherein said first and second walls are of a light-transmitting material and said opening is in one of said first and second walls.

41. A test device in accordance with claim 39 wherein said first and second walls are of an opaque material, said opening is in said first wall and said second wall has a transparent zone to permit observation of said detectable change.

42. A test device in accordance with claim 39 further comprising an air-impermeable and light-impermeable support removably adhered to the exterior of said receptacle, sealing said opening.

43. A test device in accordance with claim 35 further comprising an air-impermeable, light-impermeable package receptacle to receive and encase said penetrable solid support such that said penetrable solid support being removable therefrom.

44. A test device in accordance with claim 35 further comprising a diffusion barrier restricting diffusion through said penetrable solid support to a defined path of travel communicating said reagent with said indicator.

45. A test device in accordance with claim 35 in which said reagent is a conjugate comprising a reporter group coupled to a substrate residue yet cleavable therefrom upon contact with a catalytically active hydrolase, said test device thereby being adapted for testing for the presence of said catalytically active hydrolase in a sample.

46. A test device for assaying for the presence of an analyte in a liquid sample, said test device comprising:

a solid support having a surface;

a solid-phase reagent deposited in a first region on said surface, said reagent being one which induces a chemical reaction in an indicator when said analyte is present in said sample;

a solid-phase indicator deposited in a second region on said surface, said second region non-overlapping with said first region, said indicator being one which undergoes a detectable change upon the occurrence of said chemical reaction; and means for drawing said sample across said surface from said first region to said second region.

47. A test device in accordance with claim 46 in which said solid-phase indicator is immobilized on said surface.

48. A test device in accordance with claim 46 in which said solid-phase reagent comprises a reporter group coupled to a substrate residue and cleavable therefrom upon contact with proline iminopeptidase activity, said test device thereby being adapted for testing for the presence of bacterial vaginosis by assaying for the presence of enzymatically active proline iminopeptidase activity.

* * * * *